United States Patent
Leor et al.

(10) Patent No.: US 9,492,480 B2
(45) Date of Patent: Nov. 15, 2016

(54) IRON OXIDE NANOPARTICLES FOR USE IN TREATING NON-INFECTIOUS INFLAMMATORY DISORDERS

(75) Inventors: Jonathan Leor, Hadera (IL); Tamar Ben-Mordechai, Rishon LeZion (IL);
(Continued)

(73) Assignees: RAMOT AT TEL AVIV UNIVERSITY LTD., Tel Aviv (IL);
(Continued)

( * ) Notice: Subject to any disclaimer, the term of this patent is extended or adjusted under 35 U.S.C. 154(b) by 200 days.

(21) Appl. No.: 13/640,843

(22) PCT Filed: Apr. 12, 2011

(86) PCT No.: PCT/IL2011/000300
§ 371 (c)(1),
(2), (4) Date: Dec. 19, 2012

(87) PCT Pub. No.: WO2011/128896
PCT Pub. Date: Oct. 20, 2011

(65) Prior Publication Data
US 2013/0129810 A1 May 23, 2013

Related U.S. Application Data

(60) Provisional application No. 61/323,036, filed on Apr. 12, 2010.

(51) Int. Cl.
*A61K 9/14* (2006.01)
*A61K 9/127* (2006.01)
(Continued)

(52) U.S. Cl.
CPC ............... *A61K 33/26* (2013.01); *A61K 9/127* (2013.01); *A61K 9/14* (2013.01); *A61K 9/143* (2013.01);
(Continued)

(58) Field of Classification Search
None
See application file for complete search history.

(56) References Cited

U.S. PATENT DOCUMENTS 5,411,730 A * 5/1995 Kirpotin et al. ............ 424/9.322
5,427,767 A * 6/1995 Kresse ................. A61K 9/1271
424/9.32
(Continued)

FOREIGN PATENT DOCUMENTS

DE 102005059751 A1 6/2007
WO 99/55230 A1 11/1999
(Continued)

OTHER PUBLICATIONS

L Coussens, Z Werb. "Inflammation and Cancer." Nature, vol. 420, Dec. 19/26, 2002, pp. 860-867.*
(Continued)

*Primary Examiner* — Isaac Shomer
(74) *Attorney, Agent, or Firm* — Browdy and Neimark, PLLC

(57) ABSTRACT

In accordance with the present disclosure there are provided iron oxide nanoparticles for use in the treatment of non-infectious inflammatory disorders. Also provided by the present disclosure is a method of treatment of non-infectious inflammatory disorders making use of such particles, pharmaceutical compositions and kits comprising such particles.

16 Claims, 20 Drawing Sheets

(75) Inventors: Shimrit Adutler-Lieber, Bat Yam (IL);
Rimona Margalit, Givataim (IL);
Inbar Elron-Gross, Ramat Hasharon (IL); Yifat Glucksam-Galnoy, Kfar-Saba (IL)

(73) Assignees: TEL HASHOMER MEDICAL RESEARCH INFRASTRUCTURE AND SERVICES LTD, Tel Hashomer (IL)

(51) Int. Cl.
*A61K 33/26* (2006.01)
*A61K 45/06* (2006.01)
*A61K 47/48* (2006.01)
*C01G 49/02* (2006.01)

(52) U.S. Cl.
CPC ............... *A61K 9/145* (2013.01); *A61K 9/146* (2013.01); *A61K 45/06* (2013.01); *A61K 47/48815* (2013.01); *C01G 49/02* (2013.01); *Y10S 977/773* (2013.01); *Y10S 977/906* (2013.01)

(56) References Cited

U.S. PATENT DOCUMENTS

| | | | |
|---|---|---|---|
| 2005/0090732 A1* | 4/2005 | Ivkov et al. | 600/411 |
| 2006/0030619 A1 | 2/2006 | Liu et al. | |
| 2006/0142749 A1* | 6/2006 | Ivkov | 606/27 |
| 2006/0222696 A1* | 10/2006 | Okada et al. | 424/450 |

FOREIGN PATENT DOCUMENTS

| | | |
|---|---|---|
| WO | 01/13949 A2 | 3/2001 |
| WO | 2007072982 A1 | 6/2007 |
| WO | 2008008483 A2 | 1/2008 |
| WO | 2008089478 A2 | 7/2008 |
| WO | 2009040811 A2 | 4/2009 |
| WO | WO 2009040811 A2 * | 4/2009 |

OTHER PUBLICATIONS

NG Frangogiannis, CW Smith, ML Entman. "The inflammatory response in myocardial infarction." Cardiovascular Research, vol. 53, 2002, pp. 31-47.*
R Medzhitov. "Origin and Physiological Roles of Inflammation." Nature Insight Review, vol. 454, Jul. 24, 2008, pp. 428-435.*
BB Chin, SD Metzler, A Lameire, A Curcio, S Venulapalli, KL Greer, NA Petry, TG Turkington, RE Coleman, H Rockman, RJ Jaszczak. "Left Ventricular Functional Assessment in Mice: Feasibility of High Spatial and Temporal Resolution ECG-gated Blood Pool SPECT." Radiology, vol. 245 No. 2, Nov. 2007, pp. 440-448.*
A Bjornerud, L Johansson. "The utility of superparamagnetic contrast agents in MRI: theoretical consideration and applications in the cardiovascular system." NMR in Biomedicine, vol. 17, 2004, pp. 465-477.*
MG Friedrich. "Tissue Characterization of Acute Myocardial Infarction and Myocarditis by Cardiac Magnetic Resonance." Journal of the American College of Cardiovascular Imaging, vol. 1 No. 5, 2008, pp. 652-662.*
HB Na, IC Song, T Hyeon. "Inorganic Nanoparticles for MRI Contrast Agnets." Advanced Materials, vol. 21, 2009, pp. 2133-2148.*
Leor et al., "Ex vivo activated human macrophages improve healing, remodeling, and function of the infarcted heart" Circulation. 114(1 Suppl):I94-100 (2006).
Wei et al., "Magnetic Iron oxide nanoparticles: synthesis and surface functionalizing strategies" Nanoscale Res. Lett. 3: 397-415(2008).
Siglienti et al., Cytokine profile of iron laden macrophages: Implications for cellular magnetic resonance imaging. J. Neuroimmunology.173: 166-173 (2006).
International Search Report for PCT/IL2011/000300 mailed Jul. 18, 2011.
Kim et al., "Enhancement of neurite outgrowth in PC12 cells by iron oxide nanoparticles" Biomaterials 32:2871-2877 (2011).
Pauser et al., "Liposome-encapsulated superparanlagnetic iron oxide particles as markers in an MRI-guided search for tutnor-specific drug carriers" Anti-Cancer Drug Design, 12:125-135 (1997).

* cited by examiner

IRON OXIDE NANOPARTICLES FOR USE IN TREATING NON-INFECTIOUS INFLAMMATORY DISORDERS

FIELD OF THE INVENTION

This invention relates to medical uses of iron oxide nanoparticles.

BACKGROUND OF THE INVENTION

Iron oxide nanoparticles are used to label and track inflammatory and stem cells by MRI [Leor J, Rozen L, Zuloff-Shani A, Feinberg M. S, Amsalem Y, Barbash I M, Kachel E, Holbova R, Mardor Y, Daniels D, Ocherashvilli A, Orenstein A, Danon D. Ex vivo activated human macrophages improve healing, remodeling, and function of the infarcted heart. *Circulation*. (2006); 114(1 Suppl):194-100].

The most sensitive existing markers for cell labeling using MRI are superparamagnetic iron oxide (SPIO) particles. They are nontoxic and biodegradable and do not affect proliferation and multi-lineage differentiation capacity in vitro.

A review on magnetic iron oxide nanoparticles, including the synthesis and surface funtionalization strategies was provided by Wei Wu et al. [Wei W, He Q, Jiang C. Magnetic Iron oxide nanoparticles: synthesis and surface functionalizing strategies. *Nanoscale Res. Lett.* (2008); 3: 397-415].

Iron oxide nanoparticles have been described as anti-inflammatory in an in vitro pathogen-induced inflammation model induced by lipopolysaccharides (LPS) [Siglienti I, Bendszus M, Kleinschnitz C, Stoll G. Cytokine profile of iron laden macrophages: Implications for cellular magnetic resonance imaging. *J. Neuroimmunology*. (2006); 173: 166-173].

SUMMARY OF THE INVENTION

Based on the inventors' findings and in accordance with a first of its aspects, the present disclosure thus provides iron oxide nanoparticles for use in the treatment of non-infectious inflammation.

In accordance with a second of its aspects, the present disclosure provides a method for treating non-infectious inflammatory disorders in a subject, the method comprising providing a subject in need, an amount of iron oxide nanoparticles, the amount being effective to treat the non-infectious inflammatory disorders.

In yet a third of its aspects, the present disclosure provides the use of iron oxide nanoparticles for the preparation of a pharmaceutical composition for the treatment of non-infectious inflammatory disorders.

In yet a fourth of its aspects the present disclosure provides a pharmaceutical composition for the treatment of non-infectious inflammation, the composition comprising as active ingredient an amount of iron oxide nanoparticles, the amount being effective to treat the non-infectious inflammatory disorders.

Finally, in accordance with an a fifth of its aspects, there is provided a kit comprising iron oxide nanoparticles and instructions for use of the iron oxide nanoparticles for the treatment of a non-infectious inflammatory disorders.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 7A showing the fractional shortening [FS=(left ventricle (LV) diastolic diameter–LV systolic diameter)/LV diastolic diameter] at baseline (1 day after MI) and 30 d after MI, where FIG. 7B shows that after 30 d, FS was greater in animals treated with SPIO compared with control ($p=0.08$).

FIG. 8A shows a rat that had an MI and SPIO injection demonstrating decreased LV wall thickness and hypointense area in the LV (white arrow) in both scans. FIG. 8B shows a rat that had an MI and was injected with saline demonstrating decreased LV wall thickness without hypointense areas. FIG. 8C (sham surgery and SPIO injection) and FIG. 8D (sham surgery and saline injection) demonstrating normal LV wall thickness and no persistent hypointense areas.

FIG. 11A—TNF-$\alpha$, FIG. 11B—IL-1α, FIG. 11C—IL-1β, FIG. 11D—IL-6, FIG. 11E—IL-12, FIG. 11F—IL-23, FIG. 11G—INF-γ, FIG. 11H—IL-10, FIG. 11I—ANG-2, FIG. 11J—FGF, FIG. 11K—HGF, FIG. 11L—PDGF, FIG. 11M—TIMP-1, FIG. 11N—TIMP-2.

FIG. 12A-12C macrophages incubated for one day with 10 μg, 50 μg, 100 μg, respectively; FIGS. 12D-12F macrophages incubated for three days with 10 μg, 50 μg, 100 μg, respectively.

FIGS. 14A-14C mice treated with IONP, FIGS. 14D-14E control mice (treated with saline).

DESCRIPTION OF NON-LIMITING EMBODIMENTS OF THE INVENTION

Figure 1:
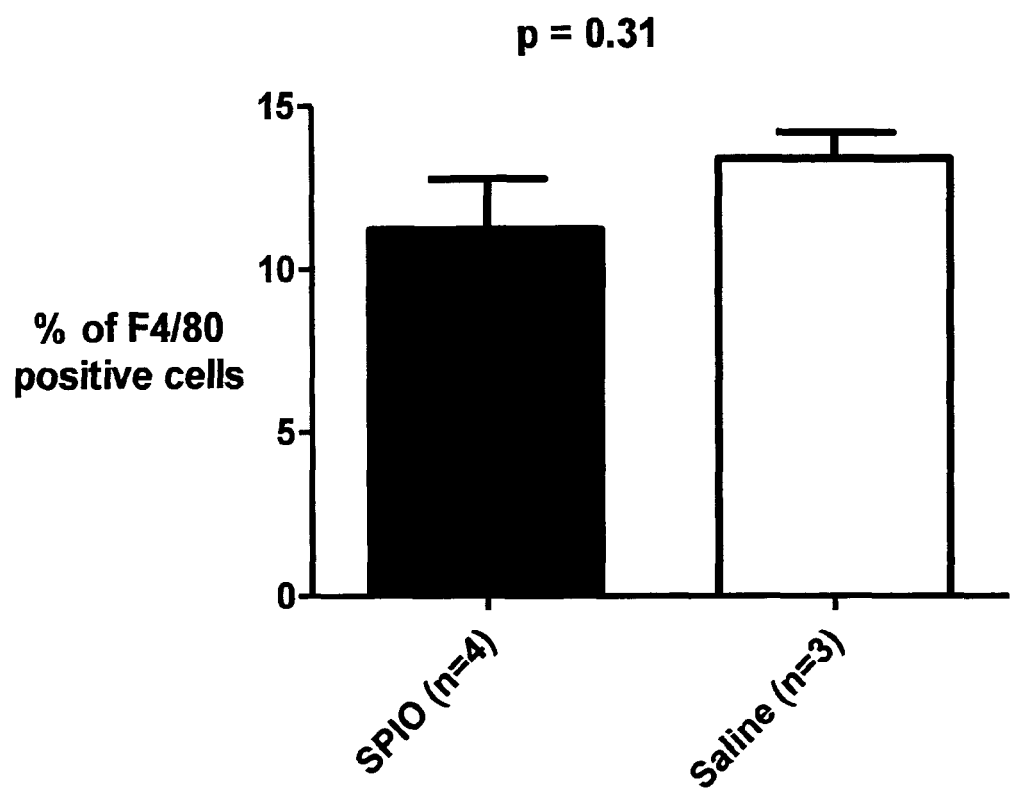
FIG. 1 is a bar graph showing the percentage of macrophages (as % of F4/80 positive cells of all infarcted heart cells) following direct injection of SPIO particles or saline (control) into the infarct; the overall number of macrophages (F4/80) in the infarcted heart was not affected by SPIO particle injection.

The present invention is based on the finding that administration of iron oxide nanoparticles can be used for the treatment of non-infectious inflammatory disorders, specifically, it was found that injection to a mouse model of MI of superparamagnetic iron oxide (SPIO) particles (ferumoxides in the non-limiting examples provided herein) at relatively low concentrations, improved cardiac function.

Macrophage is the dominant cell type in various acute conditions, such as myocardial infarction, in which macrophages control the initiation, maintenance, and resolution of inflammation. For example, one of the earliest phases after myocardial infarct (MI) involves acute inflammation leading to fibrosis and scar formation. Neutrophils and monocytes are the first to infiltrate the infarct. Monocytes become macrophages, which then take part in the acute inflammation as well as in the following healing and repair phases. Injection of activated macrophages into an infarct is associated with improved vascularization, myofibroblast accumulation, scar thickening and accumulation of resident macrophages which, in turn, contribute to infarct healing in rats.

Monocytes and macrophages display remarkable plasticity and can change their physiology in response to environmental cues. Some macrophages exhibit a pro-inflammatory cytokine profile and cytotoxic activity ("classical activation state"—M-1 polarization), whereas others show an anti-inflammatory profile and tissue repair activity ("alternative activation state" or "anti-inflammatory and reparative macrophage phenotype"—M-2 polarization). In a mouse model of myocardial infarction (MI), M-1 macrophages digested damaged tissue during the first days after MI, whereas M-2 macrophages subsequently promoted healing via myofibroblast accumulation, angiogenesis, and deposition of collagen.

In addition, macrophages actively participate in the resolution of injury and promote tissue restoration in mouse model of muscle and kidney injury.

Without being bound by theory, the inventors opine that the improved cardiac function is associated with the induction, by the iron oxide nanoparticles, of a macrophage switch from macrophage that exhibit a pro-inflammatory cytokine phenotype (the "M/polarization") to an anti-inflammatory and tissue reparative phenotype ("M2 polarization") and vice versa: from anti-inflammatory (M2) to pro-inflammatory (M1).

A macrophage in a reparative or anti-inflammatory state (also referred to as "alternatively activated macrophage") refers to macrophages displaying a Th2-like phenotype. Sometimes such state is also referred to as M-2 state or M-2 subtype and is known as promoting ECM construction, cell proliferation, and angiogenesis, this being opposed to the classically activated macrophages (sometimes referred to as M-1 state) that exhibit a Th1-like phenotype, promoting inflammation, extracellular matrix (ECM) destruction, and apoptosis.

Although both phenotypes are known to be important components of both innate and adaptive immune systems, the classically activated macrophages are known to elicit chronic inflammation and tissue injury whereas the alternatively activated macrophages are known to resolve inflammation and facilitate wound healing.

It was thus concluded that iron oxide nanoparticles can be used as a therapeutic tool to treat non-infectious inflammatory disorders by switching pro-inflammatory, classically activated macrophages (M1) to anti-inflammatory, alternatively activated (M2), reparative macrophages, and vice versa.

As used herein, the term "iron oxide" is used to denote a chemical compound composed of iron and oxygen. The iron oxide may be of any known magnetism, including, magnetic iron oxide, ferromagnetic iron oxide, ferrimagnetic iron oxide, and anti-ferromagnetic iron oxide, wherein the iron may be composed of one or both of ferric iron ($Fe^{3+}$) and ferrous iron ($Fe^{2+}$). Non-limiting examples of iron oxides include FeO (wüstite), $Fe_3O_4$ (magnetite, $Fe^{II}Fe^{III}_2O_4$) and $Fe_2O_3$ (hematite) having different forms such as, $\alpha$-$Fe_2O_3$, $\beta$-$Fe_2O_3$, $\gamma$-$Fe_2O_3$ (maghemite) and $\epsilon$-$Fe_2O_3$.

As used herein "iron oxide nanoparticles" are iron oxide containing nanoparticles having a diameter in the nanometer scale, typically ranging between 1 nm to 500, at times 1 nm to 200 nm, at preferably between 1 nm to 150 nm or even 1 nm to 100 nm. Typically, such nanoparticles are superparamagnetic particles.

The iron oxide nanoparticles may be present as naked iron oxide nanoparticles, i.e. particles comprised primarily only of the iron oxide entities, may be surface modified particles; as well as iron oxide nanoparticles within a carrier, such as hydrogels, liposomes, shell coating etc, as further discussed below.

According to some embodiments, iron oxide nanoparticles are surface modified. Surface modification may comprise coating of the surface. In this connection, and as may be appreciated by those versed in the art, iron oxide nanoparticles have a large hydrophobic surface area-to-volume ratio, and are thus susceptible to aggregation and formation of large clusters. Thus, surface coating of iron oxide nanoparticles may, on one hand prevent such aggregation, and on the other hand serve as "functionalized surface" so as to improve biocompatibility and biodegradable properties.

According to some embodiments, the iron oxide nanoparticles may be modified with organic materials for example such as small molecules, surfactants, polymers and biological molecules.

Small molecules may include without being limited thereto, amino acids, citric acids, vitamins, cyclodextrin, and surfactants may include, without being limited thereto, fatty acids, linear or branched alkyl phenols, ammonium salts, polyols and lycine. Examples include oleic acid, lauric acid, alkyl phosphonates such as dodecyl phosphonate, hexadecyl phosphonate, dihexadecyl phosphonate, Polymers may be selected for example from natural polymer such as for example dextran, starch, gelatin, chitosan; or from synthetic polymers such as for example polyethylene glycol (PEG), polyvinyl alcohol (PVA), polylactide acid (PLA), alginate, polyacrylic acid (PAA), polymethylmethacrylate (PMMA).

Biological molecules may be for example protein, polypeptides, antibody, biotin and avidin.

According to some other embodiments, the iron oxide nanoparticles may be surface modified with inorganic materials for example such as silica (e.g. $SiO_2$), metal or nonmetal elementary substances, metal oxides and metal sulfides.

Metal and nonmetal elementary substances may include, without being limited thereto, gold, silver, platinum, palladium, iron and carbon.

Metal oxides and metal sulfides may be, for example, ZnO, MgO, CaO, $SnO_2$, $Al_2O_3$, iron oxides, CoO, NiO, $CoFe_2O_4$, $TiO_2$, ZnS, $Y_2O_3$.

In yet, according to some other embodiments, the iron oxide nanoparticles may be in the form of a core and a shell coating. In one embodiment the iron oxide compound form a core within a shell of organic or inorganic material; in another embodiment, the core is of organic or inorganic material within a shell of iron oxide; in another embodiment the nanoparticles form a mosaic form; or, in yet other embodiments, the particles are in a form of a shell-core-shell or of a bi-functional dumbbell form. All these forms are well known to those versed in the art.

The surface modification may be of in any form, but is preferably by chemical interactions.

As indicated above, the iron oxide nanoparticles may also be in the form of polymeric shell coating and a core, the core comprising the iron oxide entities. Without being limited thereto, the polymeric shell coating may be comprised of one or more polymer selected from the group consisting of polysaccharide, polyethyleneglycol, dextran, carboxydextran, siloxanes, alginate (e.g. sodium alginate, calcium alginate, alginate sulfate) coating. A particular polymer according to this embodiment is dextran.

In other embodiments, the iron oxide nanoparticles may be composed of a hydrogel embedding iron oxides. The term "hydrogel" refers to a class of highly hydratable polymer materials typically composed of hydrophilic polymer chains, which may be naturally occurring, synthetic or semi synthetic and crossed linked (fully or partially).

Synthetic polymers that are known to form hydrogels include, without being limited thereto, poly(ethylene oxide) (PEO), poly(vinyl alcohol) (PVA), poly(acrylic acid) (PAA), poly(propylene fumarate-co-ethylene glycol) (P(PF-co-EG)), and polypeptides. Representative naturally occurring, hydrogel forming polymers include, without being limited thereto, agarose, alginate, chitosan, collagen, fibrin, gelatin, and hyaluronic acid (HA). A subset of these hydrogels include PEO, PVA, P(PF-co-EG), alginate, hyaluronate (HA), chitosan, and collagen.

Iron oxide nanoparticles within hydrogels may be prepared using a Sol-Gel approach for coating the SPIO with uniform shells of amorphous silica.

In some embodiments, the iron oxide within hydrogel is of the formula $Fe_2^{3+}OFe^{2+}O$.

In yet some other embodiments, the iron oxide nanoparticles are encapsulated within lipid based vesicles such as liposomes or micelles. The term "liposome" or "micelles" as used herein has the meaning acceptable in the art. A liposomes' membrane is a bilayer membrane and the membrane may include a variety of physiologically acceptable liposome-forming lipids. As used herein, the term "liposome forming lipids" means primarily glycerophospholipids and sphingomyelins. The glycerophospholipids have a glycerol backbone wherein at least one, preferably two, of the hydroxyl groups at the head group is substituted by one or two of an acyl, alkyl or alkenyl chain, a phosphate group, or combination of any of the above, and/or derivatives of same and may contain a chemically reactive group (such as an amine, acid, ester, aldehyde or alcohol) at the head group, thereby providing the lipid with a polar head group. The sphingomyelins consists of a ceramide unit with a phosphorylcholine moiety attached to position 1 and thus in fact is an N-acyl sphingosine The phosphocholine moiety in sphingomyelin contributes the polar head group of the sphingomyelin.

In liposome forming lipids the acyl chain(s) are typically between 14 to about 24 carbon atoms in length, and have varying degrees of saturation being fully, partially or non-hydrogenated lipids. Further, the lipid matrix may be of natural source, semi-synthetic or fully synthetic lipid, and neutral, negatively or positively charged.

Examples of liposome forming glycerophospholipids include, without being limited thereto, glycerophospholipid. phosphatidylglycerols (PG) including dimyristoyl phosphatidylglycerol (DMPG); phosphatidylcholine (PC), including egg yolk phosphatidylcholine, dimyristoyl phosphatidylcholine (DMPC), 1-palmitoyl-2-oleoylphosphatidyl choline (POPC), hydrogenated soy phosphatidylcholine (HSPC), distearoylphosphatidylcholine (DSPC); phosphatidic acid (PA), phosphatidylinositol (PI), phosphatidylserine (PS), phosphatiydyl ethanolamine (PE).

As appreciated, the liposome forming lipids may also include cationic lipids (monocationic or polycationic lipids). Cationic lipids typically consist of a lipophilic moiety, such as a sterol or the same glycerol backbone to which two acyl or two alkyl, or one acyl and one alkyl chain contribute the hydrophobic region of the amphipathic molecule, to form a lipid having an overall net positive charge. Preferably, the headgroup of the lipid carries the positive charge. Monocationic lipids may include, for example, 1,2-dimyristoyl-3-trimethylammonium propane (DMTAP) 1,2-dioleyloxy-3-(trimethylamino) propane (DOTAP); N-[1-(2,3,-ditetradecyloxy)propyl]-N,N-dimethyl-N-hydroxyethyl ammonium bromide (DMRIE); N-[1-(2,3,-dioleyloxy)propyl]-N,N-dimethyl-N-hydroxy ethyl-ammonium bromide (DORIE); N-[1-(2,3-dioleyloxy) propyl]-N,N,N-trimethyl-ammonium chloride (DOTMA); 3β[N—(N',N'-dimethylaminoethane) carbamoly] cholesterol (DC-Chol); and dimethyl-dioctadecylammonium (DDAB). Polycationic lipids may include a similar lipophilic moiety as with the mono cationic lipids, to which spermine or spermidine is attached. These include, without being limited thereto, N-[2-[[2,5-bis [3-aminopropyl)amino]-1-oxopentyl]amino]ethyl]-N,N-dimethyl-2,3-bis[(1-oxo-9-octadecenyl)oxy]-1-propanaminium (DOSPA), and ceramide carbamoyl spermine (CCS). The cationic lipids may form part of a derivatized phospholipids such as the neutral lipid dioleoylphosphatidyl ethanolamine (DOPE) derivatized with polylysine to form a cationic lipopolymer.

Other lipids suitable for liposome formation may include glycolipids and sterols, such as cholesterol.

In one embodiment, the combination of lipids includes PC and PE at a mole ratio of 95:5 and a total lipid concentration of 10-100 mg/ml. To this cholesterol may be added as well as phosphatidyl glycerol (PG), preferably, with PE amount not exceeding 20% mole. The amount of cholesterol is typically (if present) in the range of 5% to 30%.

The vesicle-forming lipids and their combination may be selected to achieve a specified degree of rigidity, to control the stability of the liposome in serum and to control the rate of release of the entrapped agent in the liposome. It is required that the liposome forming lipids provide rigidity to the resulting membrane, so as to prevent undesired leakage of the iron oxides from the liposomes. The addition of cholesterol may assist in manipulating the rigidity/fluidity as desired.

The components of the lipid based vesicle may be selected to achieve a specified degree of fluidity or rigidity, to control the stability of the vesicle during storage as well as after delivery, e.g. in serum and to control the rate of release of the iron oxide from the vesicle. Lipid based vesicles having a more rigid structure, e.g. liposomes in the gel (solid ordered) phase or in a liquid crystalline fluid (liquid disordered) state, are achieved by incorporation of a relatively rigid lipid, for example, a lipid having a relatively high solid ordered to liquid disordered phase transition temperature, such as, above room temperature. Rigid, i.e., saturated, lipids having long acyl chains, contribute to greater membrane rigidity in the assembly. Lipid components, such as cholesterol, are also known to contribute to rigidity in lipid structures especially to reduce free volume thereby reducing permeability. Similarly, high lipid fluidity is achieved by incorporation of a relatively fluid lipid, typically one having a relatively low liquid to liquid-crystalline phase transition temperature, for example, at or below room temperature, more preferably, at or below the target body temperature.

The lipid based vesicles may be prepared by various methods known in the art. One procedure involves dissolving a mixture of liposome-forming lipids in a suitable organic solvent and evaporating the organic solvent in a vessel to form a thin film. The film is then covered with an aqueous medium containing the iron oxides that will form the aqueous phase in the liposome interior spaces. After liposome formation, the vesicles are sized according to known methods (e.g. as sonication) to achieve a size distribution of liposomes within a selected range (preferably uniformly sized).

The liposomes encapsulating the iron oxide may be prepared as multilamellar vesicles (MLV), e.g. by solvent injection, lipid hydration, reverse evaporation, freeze drying or by repeated freezing and thawing. Yet, small (<100 nm) or large (>100 nm) unilamellar vesicles (SUV or LUV, respectively) may be prepared e.g. by sonication, by extrusion through polycarbonate filters having a defined pore size, by using a French pressure cell, i.e., by passing MLV through small orifice under high pressure, or by solvent injection methods, with solvents such as ethers or alcohols. Other types of vesicles which may be formed include unilamellar vesicle (ULV), large unilamellar vesicles (LUV); stable plurilamellar vesicles (SPLV), oligolamellar vesicles (OLV) whether prepared by detergent removal using dialysis, column chromatography, bio-beads SM-2, by reverse phase evaporation (REV); intermediate sized unilamellar vesicles formed by high pressure extrusions or giant multivesicular vesicles (MVV or GMVV, U.S. Pat. No. 6,162,462) liposomes, at least 1 microns in diameter, prepared by vortexing a lipid film with an aqueous solution of a suitable salt (e.g. ammonium sulfate), homogenizing the resulting suspension to form a suspension of small unilamellar vesicles (SUV), and repeatedly freeze-thawing said suspension of SUV in liquid nitrogen followed by water to form the MVV. All these and other methods of liposome preparation, known in the art.

In one embodiment, the liposomes are multilamellar vesicles (MLV) prepared by the thin-film method as described hereinbelow in connection with the non-limiting example.

The liposomes may be coated by targeting moieties. The targeting moiety may be a small molecular weight compound (e.g. mono or disaccharide) as well as a macromolecule (e.g. protein, polysaccharide) associated with the liposomes either by covalent or non-covalent interactions. In one embodiment, the targeting moiety is an antigen targeted to a macrophage receptor. In accordance with yet another embodiment, the liposomes are coated with hyaluronic acid (HA). It is known that HA coating may assist in targeting liposomes to the hyaluronan receptors (particularly the CD44 family) at the macrophage surface.

Iron oxide nanoparticles having a polymeric shell coating may also be classified by their size, as large iron oxide nanoparticles (about 20 nm to 3,500 nm in diameters, e.g. Ferumoxsil or AMI-121, Ferucarbotran, OMP), standard iron oxide nanoparticles (e.g. Ferumoxides or AMI-25, SHU 555A), ultrasmall iron oxide nanoparticles (e.g. Ferumoxtran or AMI-277, NC100150, in the range of 30 nm) and monocrystalline iron oxide nanoparticles (MION). In one particular embodiment, the polymer coated iron oxide nanoparticles have a diameter of between 4 nm and 200 nm.

In one embodiment, the iron oxide nanoparticles are Ferumoxides which are nanoparticles composed of iron particles of about 5 nm, the iron crystalline particles being covered with a layer of dextran and have a hydrodynamic diameter of about 80-150 nm Ferumoxides are classified as SPIO.

Further, when referring to iron oxide nanoparticles within a polymeric shell coating, such may be prepared by controlling the precipitation of iron oxide in an aqueous solution of ferric salt, ferrous salt, and coating material by addition of an alkaline solution while active stirring or sonication. The desired iron oxide nanoparticles size may be isolated and purified by differential column chromatography, centrifugation, and dialysis. Electron microscopy, X-ray diffraction and laser light scattering which may be used to measure median diameter of the resulting nanoparticles.

The iron oxide nanoparticles are formulated into a pharmaceutical formulation with a physiologically acceptable carrier, which is typically, an inert, non-toxic substance.

The amount of the iron oxide compounds in the formulation is typically determined in appropriately designed clinical trials (dose range studies) to achieve a desired effect and the person versed in the art will know how to properly conduct such trials in order to determine the amount. As generally known, an effective amount depends on a variety of factors including the distribution profile of the nanoparticles within the body, a variety of pharmacological parameters such as half life in the body, undesired side effects, if any, on factors such as age and gender of the treated individual etc. The amount must be effective to achieve a desired therapeutic effect such as improved survival rate or more rapid recovery of the treated subject, or improvement or elimination of symptoms and other indicators associated with the inflammation under treatment, selected as appropriate measures by those skilled in the art.

In some embodiments the amount of the iron oxide nanoparticles is considered to be a low amount such that in in vitro assays, an anti-inflammatory effect is achieved, while an increase in the amount above a threshold, a pro-inflammatory behavior of the macrophages is exhibited. In some embodiments, the amount is lower than 200 µg, at times lower than 100 µg, e.g. between 20 µg to 100 µg, or between 20 µg to 50 µg. At such concentrations, an increase of CD206 and CD163, markers of anti-inflammatory M2-type human macrophages are exhibited. Yet, at times, at the above recited amounts, an increase in IL-10 is exhibited, being a cytokine characterizing, in some non-infectious inflammations, an anti-inflammatory activity.

The iron oxide nanoparticles are administered and dosed taking into account the clinical condition of the individual, the site and method of administration, scheduling of administration, patient age, sex, body weight and other factors known to medical practitioners. The dosage form may be single dosage form or a multiple dosage form to be provided over a period of several days. The schedule of treatment with the nanoparticles generally has a length proportional to the length of the non-infectious inflammatory process, the parameters of the individual to be treated (e.g. age and gender) and the effectiveness of the specific iron oxide nanoparticles employed.

The iron oxide nanoparticles can be administered orally, subcutaneously (s.c.) or parenterally including intravenous (i.v.), intraarterial (i.a.), intramuscular (i.m), intraperitoneally (i.p) and intranasal (i.n) administration as well as by infusion techniques.

In one embodiment, the iron oxide nanoparticles are formulated with a physiologically acceptable carrier suitable for systemic delivery, i.e. by injection of the particles into the bloodstream where they are engulfed by activated macrophages at site of e.g. inflammation or the wound where, without being bound by theory, it is believed that the particles induce the macrophages to adopt a reparative phenotype, i.e. the alternative activated state, M2 polarization state.

In some other embodiments, the particles are delivered locally by injection to the target site, e.g. of inflammation or of a wound. Also in accordance with this embodiment, the particles are believed to be engulfed by activated macrophages in situ of e.g. inflammation where the particles induce the macrophages to adopt a reparative phenotype. In the context of the present invention, the term "target site" is used to denote tissue or organ that is either inflamed (sterile inflammation); or tissue that is injured for example a wounded tissue or an ischemic tissue.

In this context, the present disclosure thus also provides a method of treatment non-infectious inflammatory disorders comprising administering to a subject in need of treatment of a non-infectious inflammatory disorders of an amount of iron oxide nanoparticles, the amount being effective to treat the non-infectious inflammatory disorders.

Further, in this context, the present disclosure provides the use of iron oxide nanoparticles for the preparation of a pharmaceutical composition (formulation) for the treatment of non-infectious inflammatory disorders, as well as such compositions.

As used herein the term "treatment" is understood to refer to obtaining a desired pharmacological and physiological effect. The effect may be prophylactic in terms of preventing or partially preventing the development of non-infectious inflammatory disorders or the effect may be therapeutic in terms of healing, ameliorating or reducing the non-infectious inflammatory disorders, such as the amelioration, or reduction of an inflammatory response, e.g. when relating to the activated macrophage mediated disorder, and/or healing damaged tissue for example wound healing. In some embodiments, treatment includes curing (partially or fully) of damaged (injured) tissue, tissue regeneration, tissue remodeling.

In some embodiments the treatment may involve promoting macrophages to shift to a reparative or anti-inflammatory state thereby treating the non-infectious inflammatory disorders. In this context, the non-infectious inflammatory disorders may be a type inflammation medicated by activated macrophage.

As used herein, the term "non-infectious inflammatory disorders" used interchangeably with the term "sterile inflammatory disorders" is to be understood as encompassing any immune response that is not related to activation of the immune system, e.g. by an infection. Such non-infectious inflammatory disorders denote any disorder which the activation of macrophages or activated macrophages play a role such as auto-immune disorders and inflammatory disorders which are not infection related, i.e. non-pathogenic, caused by other than an infectious agent (e.g. auto-antigen, hypersensitivity, wound). Illustrating but not limiting examples of such activated macrophage-related, non-infectious inflammatory disorders are inflammatory diseases of the gastrointestinal tract such as Crohn's disease, inflammatory bowel disease, gastritis, colitis, ulcerative colitis, colon irritable, gastric ulcer and duodenal ulcer, inflammatory diseases of the skin such as psoriasis, inflammatory diseases of the respiratory system such as asthma, allergic rhinitis or chronic obstructive pulmonary disease (COPD), pulmonary fibrosis, sarcoidosis, inflammatory diseases of the musculoskeletal system such as rheumatoid arthritis, osteomyelitis, osteoporosis, or neuritis, systemic sclerosis, inflammatory diseases of the kidneys such as glomerulonephritis, renal ischemia, or renal inflammation; inflammatory diseases of the nervous system such as multiple sclerosis, Alzheimer's disease and HIV-1-associated dementia; auto-immune diseases such as diabetes, type 1 and 2 diabetes mellitus and graft versus host reaction; infectious disease such as nephritis, sepsis, septic shock, endotoxic shock, adult respiratory distress syndrome; inflammatory conditions of the cardiovascular system, such as myocardial infarction, myocarditis, atherosclerosis, hypertensive cardiomyopathy, atheroma, intimal hyperplasia or restenosis.

The non-infectious inflammatory disorders also denote tissue healing and repair. The tissue may be injured or damaged as a result of ischemia or necrosis. Non-limiting examples of tissue damage may include infracted myocardium, myositis, myocarditis, myocardial fibrosis, glumerulonephritis, diabetic nephropathy, kidney infarct, glomerular sclerosis, stroke, liver injury, brain injury, pulmonary fibrosis, ischemic limb, athrosclerosis vascular disease, chronic ulcer.

The non-infectious inflammatory disorders may be acute non-infectious inflammatory disorders or chronic non-infectious inflammatory disorders.

It is specifically noted that the non-infectious inflammatory disorders exclude any phatogenic, e.g. bacterial, mediated inflammation (e.g. due to pathogenic infection).

In one embodiment, the non-infectious inflammatory disorders may be involved in a condition selected with tissue injury, infarct, trauma, and necrosis. According to some embodiments, the non-infectious inflammatory disorders are associated with a damaged tissue condition, for example healing a wounded tissue.

In one additional embodiment, the non-infectious inflammatory disorders are of the cardiovascular system, such as, myocardial infarction (MI), acute MI (commonly known as heart attack), myocarditis and atherosclerosis.

The administration of the iron oxide nanoparticles may be in combination with one or more other active agents, such as one or more anti-inflammatory agents. Examples of anti-inflammatory agents which may be combined with the iron oxide particles include, without being limited thereto, steroidal anti-inflammatory drugs and non-steroidal anti-inflammatory drugs (NSAID). The additional agent may be administered to the subject before, concomitant or after administration of the iron oxide nanoparticles. When administered together with the iron oxide particles, the two (or more) may be in the same formulation or formulated in two different formulations.

The iron oxide nanoparticles such as those defined herein may form part of a therapeutic kit for use by a practitioner, e.g. a medical doctor, a nurse, or by a subject in need of the treatment. The kit may comprise the iron oxide nanoparticles within a physiologically acceptable carrier, or the particles and the physiologically acceptable carrier to be combined (mixed) prior to use, and instructions for use of the iron oxide nanoparticles with the physiologically acceptable carrier for administering to the subject, typically by injection. The kit may comprise a single dosage unit of the iron oxide nanoparticles for single administration or may comprise multiple dosages of the particles, e.g. for multiple, sequential administrations according to a predefined schedule of treatment.

The invention will now be exemplified in the following description of experiments that were carried out in accordance with the invention. It is to be understood that these examples are intended to be in the nature of illustration rather than of limitation. Obviously, many modifications and variations of these examples are possible in light of the above teaching. It is therefore, to be understood that within the scope of the appended claims, the invention may be practiced otherwise, in a myriad of possible ways, than as specifically described hereinbelow.

As used herein, the forms "a", "an" and "the" include singular as well as plural references unless the context clearly dictates otherwise. For example, the term "an iron oxide nanoparticle" includes one or more nanoparticles. Further, as used herein, the term "comprising" is intended to mean that the composition include the recited iron oxide nanoparticle, e.g. SPIO particles, but not excluding other elements, such as physiologically acceptable carriers and excipients as well as other active agents. The term "consisting essentially of" is used to define compositions which include the recited elements but exclude other elements that may have an essential significance on the desired treatment. "Consisting of" shall thus mean excluding more than trace elements of other elements. Embodiments defined by each of these transition terms are within the scope of this invention.

NON-LIMITING EXAMPLES

Materials and Methods

This study was performed in accordance with the guidelines of The Animal Care and Use Committee of the Sheba Medical Center, Tel-Aviv University, which conforms to the policies of the American Heart Association and the Guidelines for the Care and Use of Laboratory Animals (Department of Health and Human Services, NIH Publication no. 85-23).

Iron Oxide nanoparticle (IONP)

Ferumoxide (Endorem; Guerbet, Villepinte, France) which has been approved as a contrast agent for liver lesion MRIs similar to Feridex [Leor J, Gerecht S, Cohen S, Miller L, Holbova R, Ziskind A, Shachar M, Feinberg M. S, Guetta E, Itskovitz-Eldor J. Human embryonic stem cell transplantation to repair the infarcted myocardium. Heart. (2007); 93(10): 1278-1284], was used as an IONP source. Ferumoxide is an iron oxide nanoparticle solution provided with a total iron content of 11.2 mg/mL.

Mouse Model of Acute Myocardial Infarction (AMI)

Balb C female mice (12 weeks, 20-25 g) were anesthetized with 2% isoflurane. The chest was opened by left thoracotomy through the fourth intercostal space to expose the beating heart. The left main coronary artery was permanently occluded with an intramural suture.

Injection of Iron Oxide nanoparticle

Ferumoxide (20 µl, 224 µg) or saline (20 µl) was injected into the infarcted mouse heart soon after coronary artery occlusion.

Isolation and Characterization of Infarct Macrophages

Mice were killed with $CO_2$, hearts were harvested and went through three 10-minute cycles of a digestion enzyme cocktail [Itzhaki-Alfia A, Barbash I. M, Raanani E, Steprnik L, Spiegelstein D, Netser S, Holbova R, Lavee J, Leor J. Patient Characteristics and Cell Source Determine the Number of Isolated Human Cardiac Progenitor Cells. *Circulation Research*. (2009); 105(7): P153]. The purified cells were centrifuged and processed for subsequent fluorescence-activated cell sorting (FACS) and enzyme-linked immunosorbent assay (ELISA) analysis.

Isolation and Characterization of Peritoneal Macrophages

Thioglycollate (Hy-labs) was injected IP into mice. Three days later mice were anesthetized with 2% isoflurane, sterile PBS (2 ml) was injected into the abdominal cavity and the peritoneal fluid was aspirated and centrifuged. The sediment was counted and cultured. To determine the effect of iron oxide nano particles on peritoneal macrophage secretion, $0.5 \times 10^6$, macrophages were cultured with 25 µg or 50 µg SPIO particles (ferumoxides; Endorem; Guerbet, Villepinte, France). Three days later the medium of the cells was analyzed by ELISA.

Enzyme-Linked Immunosorbent Assay (ELISA) Peritoneal Macrophages

Levels of various cytokines in cell culture medium, collected at different time points, were measured in triplicate with commercially available kits (R&D, McKinley Place Nebr., Minneapolis, Minn., USA, supplying antibodies against mouse TNFα, TGFβ and IL-10) of sandwich ELISAs and Q-Plex arrays, enabling measurements of up to 16 cytokines at once (Quansys biosciences multiplex ELISA, West Logan, Utah, USA, supplying antibodies against human TNFα, IL-1α, IL-1β, IL-6, IL-12, IL-23, IL-10, ANG-2, FGF, HGF, PDGF, TIMP-1).

Collected cell culture mediums were incubated with capture antibodies (provided in the kits detailed above) overnight.

After medium/fluid addition, biotinylated detection antibodies (provided in the kits detailed above) were added followed by Streptavidin-HRP and substrate (provided in the kits detailed above) for optical density measurement by spectrophotometer or light measurements and analysis using Q-View imager and software (http://www.quansysbio.com/products-services/q-view-imager).

Flow Cytometry (FACS).

Isolated peritoneal or heart cells were suspended in FACS wash buffer and Fc block for 20 minutes at 4° C. Cells were stained with APC conjugated anti-mouse F4/80 (BioLegend) and with either PE conjugated anti-mouse CD86 (as M1 marker; BioLegend) or FITC conjugated anti-mouse mannose receptor (CD206; as M2 marker; BioLegend). Single-cell suspension was prepared for cell cytometry analysis Preparation includes staining with antibodies and pipetting through a mesh filter attached above FACS tube to prevent cell aggregates.

Cells were analyzed on a FACS Calibur cytometer (BD Bioscience) using CellQuest software (BD Bioscience).

Echocardiographic Examination

Echocardiography studies were performed with a commercially available mouse echocardiography system (Vevo 770, VisualSonics) equipped with 35 MHz phased array at 1 and 30 days after MI. All measurements were performed by an experienced technician, blinded to the treatment group.

Histological and Immunohistochemical Examination

One month after injection, animals were sacrificed with an overdose of phenobarbital. Hearts were harvested and processed for histological and immunohistochemical examination. Adjacent blocks were embedded in paraffin, sectioned into 5-μm slices and stained with hematoxylin and eosin. Serial sections were immunolabelled with antibodies against smooth muscle α-actin (SMA), lectin, and macrosialin (mouse CD68).

Rat Model of MI

Sprague-Dawley male rats (weight 230-250 gr.) were anesthetized using a combination of ketamine (50 mg/kg) and xylazine (10 mg/kg), intubated and mechanically ventilated. The chest was opened by left thoracotomy and the pericard was dissected. The proximal left coronary artery was occluded using an intramural stitch (6-0 Prolene). A second group of rats underwent sham surgery (n=9) without occlusion of the artery and served as the control group.

Intravenous Delivery of SPIO into the Infarcted Heart of Rat

Thirteen rats underwent surgery to induce a myocardial infarction and 9 underwent sham surgery. All rats were injected IV with either SPIO (18 mg/Kg of Endorem®; Guerbet, Villepinte, France) or the same volume of saline 0.9% 48 hours after the procedure.

On days 6 and 10 rats underwent MR imaging (0.5T GE iMRI). Imaging sequences included T1 spin echo and T2* gradient echo.

The rats were then killed and the hearts processed for histology. Sections were stained with hematoxylin and eosin (H&E; Sigma Aldrich, Rehovot, Israel), Prussian blue staining for iron particles detection and immuno-labeled with antibodies against ED1 (AbD Serotec, NC, USA), a marker for tissue-resident macrophages.

SPIO Tracking by MRI

It is established that the peak period of macrophage activity in an infarcted rat heart is between days 2-7. Hence, 4 days after the infarction, the rats were injected with SPIO. They were anesthetized and ventilated as previously described and the right internal jugular vein was exposed. Some of the rats were injected with 18 g/kg of SPIO (ferumoxides; Endorem®; Guerbet, Villepinte, France) to a total volume of 2.5 cc as a slow push injection while others were injected with a comparable volume of isotonic saline. Due to a half life of ~10 hours in other organs (such as liver and bladder) the rats underwent imaging 48 hours after the injection (day 6 after the MI) and again on day 10 post MI. We used a 0.5T GE iMRI with a specially constructed animal probe for imaging. Imaging sequences included T1 spin echo, T2* gradient echo. Since the slice thickness of the 0.5T MR system is limited to slices of 3 mm, the T2* gradient echo was acquired twice with a shift of 1.5 mm, enabling better registration between different scans.

Histology

After the second imaging the rats were euthanized and their hearts were excised and sectioned along the short-axis plane, fixed in formalin and later embedded in paraffin. Sections were then stained with hematoxylin and eosin (H&E), Prussian blue staining for iron particle detection and immunolabeled with antibodies against ED1 (Serotec), a marker for tissue-resident macrophages. A double staining for ED1 and iron was performed in order to establish that the iron was contained by macrophages.

MRI Analysis and Histological Correlation

All MR images were analyzed and presented to a senior experienced imaging researcher in an unbiased manner in order to point out areas suspicious for containing SPIO (hypointense spots on T2* weighted MRI). These areas were correlated with the histological slides. Suspicious areas were first examined for the presence of MI using the H&E staining. In the second phase a comparison was made between the areas suspected of containing SPIO in the MR images and the slides stained for iron. Then double-staining slides were used for ED1 and iron in order to establish the presence of iron-containing macrophages in the suspicious areas.

Statistical Analysis

All variables are expressed as mean±SEM. Parametric values were compared with unpaired student t test and ANOVA (GraphPad Software, San Diego, Calif.).

Differences in cytokine levels in cultured medium at different days were compared with two-way ANOVA.

Isolation of Human Monocytes

Leukocyte blood units were purchased from an Israeli blood bank (Magen David Adom, Israel). Each donor signed an informed consent form prior to donating blood.

Peripheral blood mononuclear cells (PMNC) were isolated from human leukocyte blood units, using Ficoll membrane tubes (UNI-SEP$_{MAXI}$ NovaMed, Chicago, Ill., USA). Red blood cells (RBCs) were lysed using RBC Lysis Solution (Biological Industries, Beit Haemek, Israel), according to the manufacturer's instructions.

CD14+ monocytes were positively selected from PMNCs using Mini MACS (Miltenyi Biotec, Bergisch Gladbach, Germany). Mouse anti-human CD14-FITC (Miltenyi Biotec, Bergisch Gladbach, Germany) was used for purity validation using Flow Cytometry (Calibur flow cytometer), and Flowjo software. CD14 negative cells were used as a control group.

Co-culturing of Macrophages and IONPs

In order to assess dose dependency, different amounts of Endorem were used for macrophage incubation.

Isolated human monocytes were cultured for 5 days in RPMI (Gibco-Invitrogen, Carlsbad, Calif., USA) supplemented with 10% FBS (Biological Industries, Beit Haemek, Israel), and 1% pen-step (Biological Industries, Beit Haemek, Israel).

On the fifth day medium was refreshed and adherent macrophages were incubated for 1 to 14 days with different concentrations of SPIO between 5-500 μg of IONPs (Endorem).

Flow Cytometry (FACS) Analysis of Macrophages

At indicated time points, macrophages were detached from the surface using a scraper, washed and stained with saturating concentrations (namely, counting the cells and staining according to the manufacturers' instructions of saturating amount of Antibodies per $10^6$ cells) of FITC conjugated human anti-mouse mannose receptor (CD206) (BioLegend, San-Diego, Calif., USA) and with APC conjugated human anti-mouse CD163 (BioLegend, San-Diego, Calif., USA).

Single-cell suspension was prepared for cell cytometry analysis. Negative control comprised isotype for each sample. Samples were analyzed with a FACSCalibur cytometer (BD Bioscience). Data analysis was performed using Flowjo software (by "Tree Star"—http://www.flowjo.com/home/agreement.html)

Phagocytosis Assay

Phagocytic ability was assessed by measuring the percentage of the macrophage which phagocytised fluorescent beads by measuring the fluorescent intensity and providing the geometric mean of their fluorescence.

Aqueous suspension with red fluorescent latex beads (2.5% solids, mean diameter 1 µm, amine modified polystyrene, Sigma-Aldrich, Rehovot, Israel), was used as stock suspension.

Macrophages grown on six well plates (Corning well plates, by Corning®) for 5-7 days were washed with PBS and then with 2 ml of fresh RPMI containing 5 beads per adherent cell was added (10% FBS, 1% PS).

Plates were incubated at 37° C. for 3 h in the dark, washed with PBS 3 times and scraped. Single-cell suspension (approx. 100,000 cells) was prepared for FACS analysis using FACS-Calibur flow cytometer and Flowjo software.

Mouse Model of Wound Formation

Mice (12 w, 25-30 gr) were anesthetized with a combination of 2% isoflurane and $O_2$. A wound was created on each mouse back using a sterile 5-mm-wide biopsy punch. A few drops (20 µl) of IONP (0.224 mg IONP, 0.2M) (n=4) or saline (n=2) were topically administrated once on the wound surface immediately following wound formation.

Wounds were documented every day by camera in order to follow wound-closure.

After 12 days, mice were sacrificed and back biopsies were taken for histological analysis of Prussian blue staining for iron particles detection (Sigma Aldrich, Rehovot, Israel).

Statistical analysis

Data are presented as mean±SEM. Differences between ELISA/FACS measurements are compared with two-way ANOVA and Bonferroni post-test. A simple linear regression analysis was used to estimate the relationship between IONP dose and percentage of M2. GraphPad Prism version 5.00 for Windows (GraphPad Software, San Diego, Calif., USA) was used for analysis.

Preparation of Liposome's loaded with IONP

Liposomes are prepared according to the classical thin-film method, the base liposome is composed of phosphatidylcholine:phosphatidylethanolamine (PC:PE, the "base liposome") at the mole ratio of 95:5, and a total lipid concentration of 10-100 mg/ml. Specific liposome formulations are either the base liposome, or the base liposome with the additions of cholesterol and/or phosphatidyl glycerol (PG), with the restriction that PE concentration does not exceed 20% mole.

(a) Loading of IONP into liposomes by the thin film method.

The formed liposomes are dissolved in ethanol and evaporated to dryness in a rotary evaporator under reduced pressure to form a dry thin lipid film [Elron-Gross I, Glucksam Y, Margalit, R. Liposomal dexamethasone-diclofenac combinations for local Osteoarthritis treatment. *Intl. J. Pharma.* (2009); 376: 84-91].

The dry thin lipid film is incubated (in a shaker bath) with a swelling solution (0.1 M borate buffer at pH 9) containing IONP at amounts between 0.1 mg/ml to 10 mg/ml for 2 hours at a temperature selected from among 37°-65° C. (the temperature depending on the specific lipid composition).

Separation of excess (un-encapsulated) IONP is done by Ficoll gradient or mini (centrifuged) gel-exclusion chromatography. Buffer replacement to PBS (at physiologic pH) is done by ultracentrifugation and repeated (3-4 times) washings with PBS, or preparative dialysis against PBS. Absorption at 490 nm is used for quantitative determination of the encapsulation efficiency and encapsulated IONP dose are calculated.

(b) Loading of IONP into pre-formed free liposomes

Alternatively, liposomes are prepared as detailed above including buffer replacement however, the swelling solution contains buffer alone. The liposome suspension is frozen for 2 hours at −80° C., followed by lyophilization. The resultant liposome powders are stored at −18° C. until further use.

For IONP loading, the lyophilized liposome powder is brought to room temperature, and rehydrated back to original volume with aqueous IONP, the system is incubated for 4-24 hours at 37° C. Separation and quantitative determination are also as described above.

(c) Loading of IONP into hyaluronan (HA)-coated liposomes

Liposome preparation, IONP loading, separation and quantitative determination are essentially as described [Elron-Gross I, et al. (2009) ibid.; Peer D, Margalit R. Physicochemical evaluation of a stability-driven approach to drug entrapment in regular and in surface-modified liposomes, *Arch Biochem Biophys* (2000); 383: 185-90], with the following changes and additions (1) The IONP-loaded liposomes remain suspended in the basic borate buffer.

(2) HA is dissolved in acetate buffer (0.1 M, pH 4.5) at the concentration of 2 mg/ml, and pre-activated by incubation with ethylcarboiimide hydrochloride (EDC) (EDC:hyaluronan 20:1 v/v) for 2 hours at 37° C.

(3) At the end of the incubation the activated hyaluronan is mixed with a suspension of the IONP-loaded liposomes at the ratio of 1:1 (v/v).

(4) This reaction mixture is incubated for 24 hours in a shaker bath at 37° C. Separation from excess reagents and byproducts are by ultracentrifugation (with repeated washings in PBS) or preparative dialysis, as described above.

(d) Loading of IONP into pre-formed-free HA-coated liposomes[8]

Drug-free liposomes are prepared essentially as described above, the liposome suspension remaining at the basic buffer. Next, the liposomes are surface-coated by HA as described above, lyophilized, IONP-loaded, separated and washed as described above and quantitative determination performed as described above.

Targeting to macrophages of liposome suitable for use in IONP:

For quantitative binding (thermodynamics) 48 hours prior to an experiment the macrophages are seeded onto 24-well plates and the experiment is initiated upon 95% confluency. The cell-growth media is replaced with 500 µl of serum-free medium containing the desired liposomes at increasing concentrations. Incubations are for 60 minutes at 37° C. Upon termination, the medium from each well is aspirated, and each well is washed three times with PBS. The cells from the control wells (namely receiving no liposomes, only the serum-free medium) are lifted by trypsin and used to count the number of viable cells/well using the trypan blue method. The cells in all other wells are lysed with 1 N NaOH over night at 37° C., the content of each well collected and assayed for cell-associated liposomes. Liposome assay is by inclusion of trace [$^3$H]Cholesterol in the formulation, but other assay methods using different liposomal tags can also be applied. Wells receiving medium alone serve as controls. The results are processed according to the Langmuir isotherm, using computer-aided nonlinear regression analysis to determine how many types of binding sites the cells offer to the liposomes, as well as the affinities and capacities of each type of binding site.

For imaging and cellular localization the macrophages are grown on glass cover slips for 48 hours and the experiment is initiated upon confluency. The cells are washed with 1 ml PBS and incubated with PE-Rhodamine-labeled liposomes for 60 minutes at 37° C., followed by the addition of an anti-CD44 antibody (HCAM clone IM7) carrying a fluorescent tag (FITC or Alexa-488). Incubation is continued for 20 minutes at 4° C. Upon termination, each well is aspirated, washed with PBS and examined under a Zeiss LSM 510 Confocal microscope (magnification 40× with NA 1.2 water immersion objective). Excitation is by argon laser at 488 nm or 543 nm and emission is captured through a 525 nm or 580 nm long pass filter, for the anti-CD44 antibody and for the PE-Rhodamine labeled liposomes, respectively.

RESULTS

Results of Experiments after MI and in Peritoneal Macrophages in Mouse

Overall, 27 mice were included in the study: 10 for the effect of iron oxide on macrophage phenotype and function by FACS and ELISA; 17 for the echocardiography functional study; 1 mouse was excluded because of small infarct by echocardiography; 1 mouse died within 24 h after MI, 0 mice died during the follow-up period. Thus, the final functional analysis was carried out on 15 mice.

SPIO Switch Infarct Macrophages to Reparative Phenotype

The overall number of macrophages in the infarcted hearts was not affected by SPIO injection (FIG. 1). Two subpopulations were identified in the infarcted heart: M1, inflammatory macrophages, characterized by double staining for F4/80 and CD86, and M2, reparative, anti-inflammatory macrophages, characterized by double staining for F4/80 and CD206.

Figure 2A:
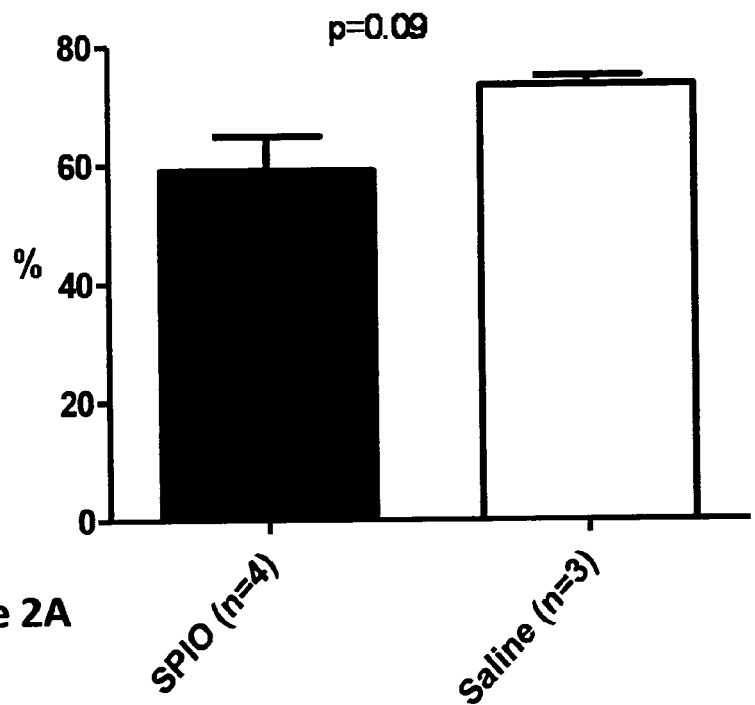
FIGS. 2A-2B are bar graphs showing percentage (% from F4/80) of pro-inflammatory (M1) macrophages (FIG. 2A) or reparative (M2) macrophages (FIG. 2B) in SPIO treated or saline (control) treated mice induced with MI. Direct SPIO injection reduced the % of M1 and increased the % of M2.
Figure 2B:
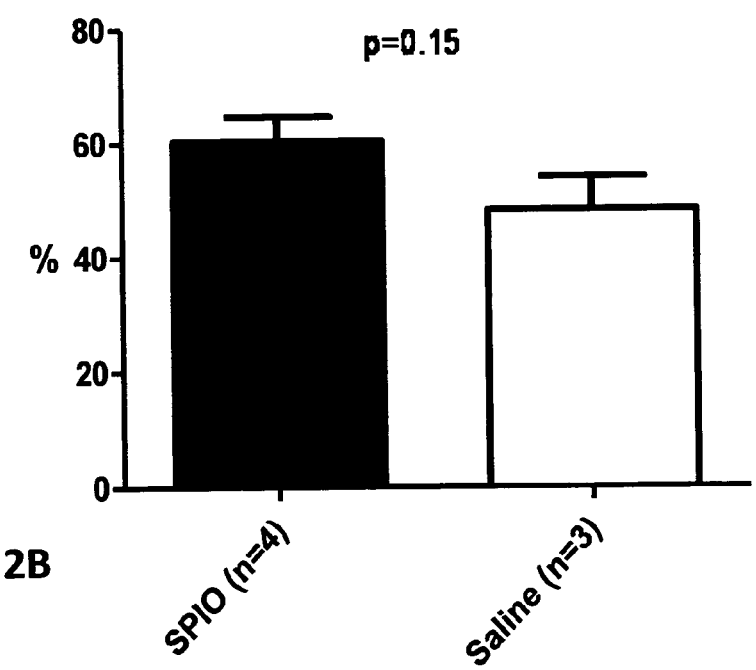
Figure 3:
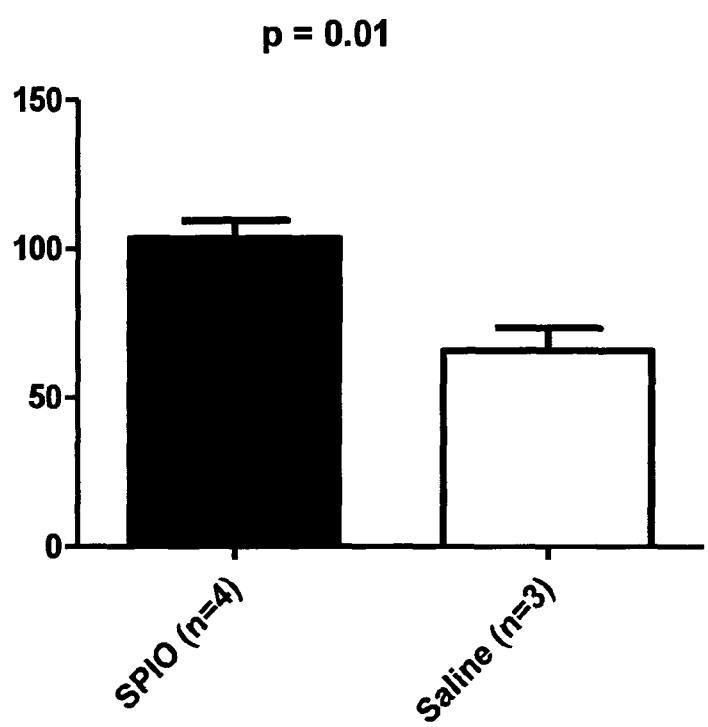
FIG. 3 is a bar graph showing the increase in proportion between reparative (M2) macrophages and pro-inflammatory (M1) macrophages in MI induced mice 72 h after injection with SPIO vs. injection with saline (control).

SPIO injection immediately after MI reduced the percentage of M1 and increased the percentage of M2 macrophages in the infarcted heart compared with control hearts, 3 days after M1 (FIG. 2). Thus, the M2/M1 ratio was significantly greater in infarcted hearts treated with SPIO compared with saline-treated hearts, 3 days after MI (p=0.01; FIG. 3).

SPIO-Modulated Infarct Macrophage Cytokine Secretion Profile

Figure 4A:
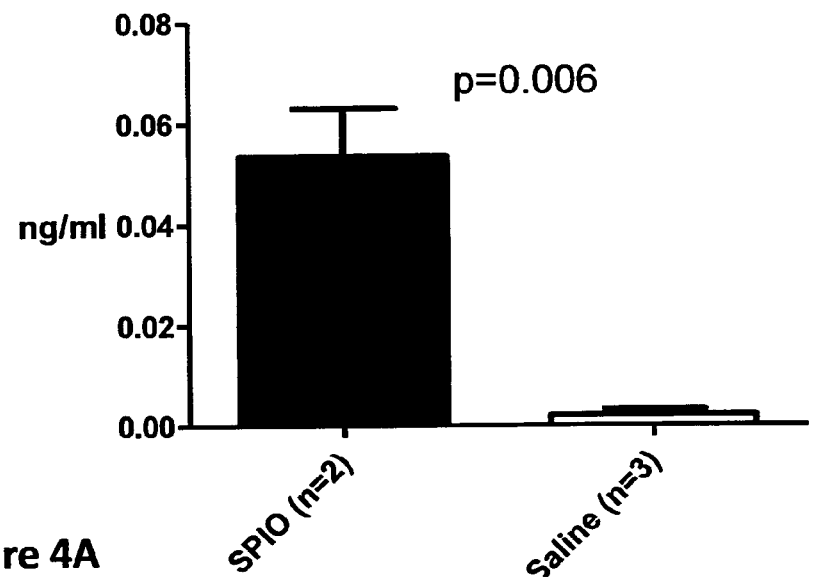
FIGS. 4A-4B are bar graphs showing cytokine secretion profile in macrophages isolated from the infracted heart of mouse and cultured, where as shown direct SPIO injection into the infarct increased TNF-$\alpha$ (FIG. 4A) and IL-10 (FIG. 4B) secretion from infarct macrophages.
Figure 4B:
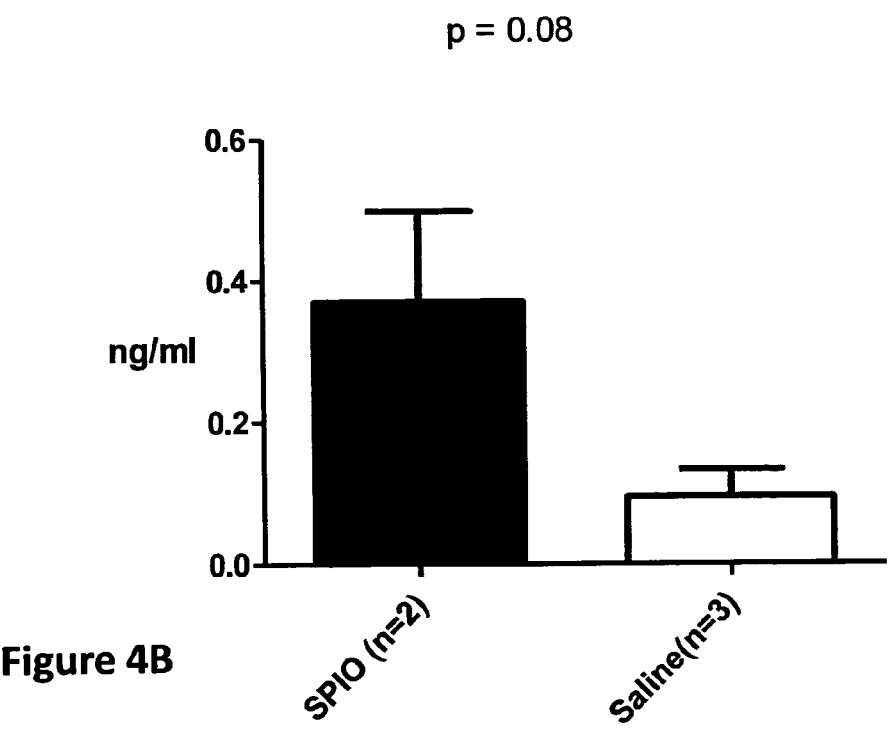

SPIO modified infarct macrophage cytokine profile. Macrophages were isolated from the infarcted heart 72 hours after MI and cultured for 24 hours. The amount of secreted TNFα and IL-10 was higher in macrophages derived from infarcted hearts treated with SPIO (FIG. 4). This is significant because IL-10 has anti-inflammatory properties and is an essential immuno-regulator that controls inflammation, healing and repair. On the other hand, TNFα is an immune cell regulator that controls both death and anti-death signaling in cardiac cells. In addition, it characterizes wound healing macrophages. TNFα released later in the inflammatory response by M2 macrophages plays an essential role in antioxidant defense and in the initiation of tissue repair [Schwabe R F, Brenner D A. Mechanisms of Liver Injury. I. TNF-{alpha}-induced liver injury: role of IKK, JNK, and ROS pathways. *Am J Physiol Gastrointest Liver Physiol.* (2006); 290(4): G583-589]. This latter activity is due to the ability of TNFα to function as a potent mitogen. Thus, depending on the situation, it could affect myocardial protection and healing.

SPIO-Modulated Peritoneal Macrophage Cytokine Secretion Profile

Figure 5:
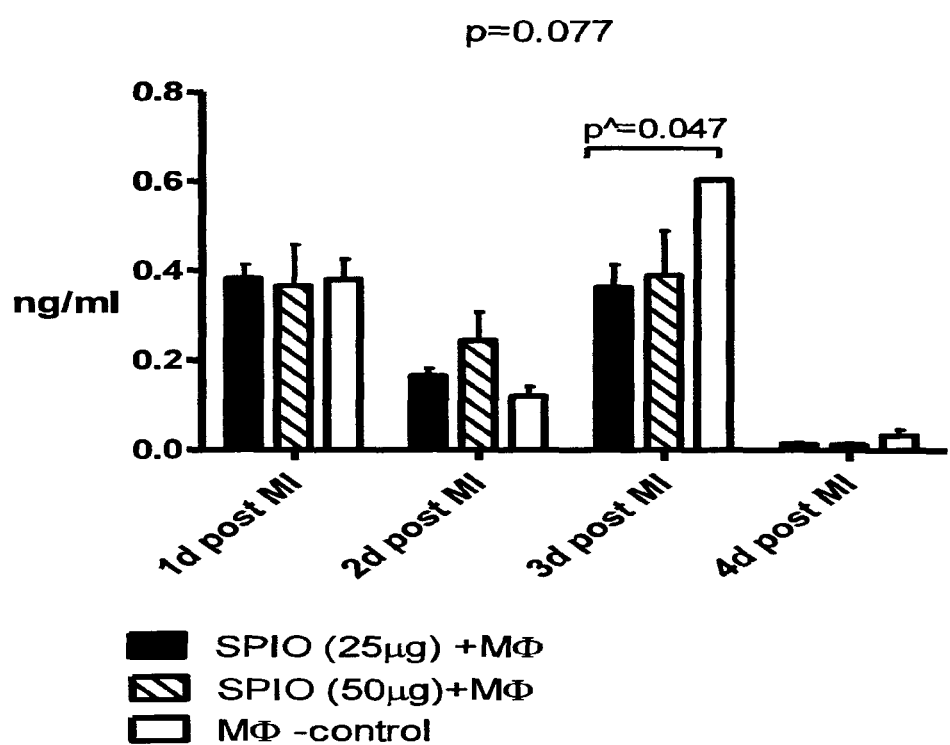
FIG. 5 is a bar graph showing that SPIO reduced TNF-$\alpha$ secretion 3 days after incubation with peritoneal macrophages.
Figure 6A:
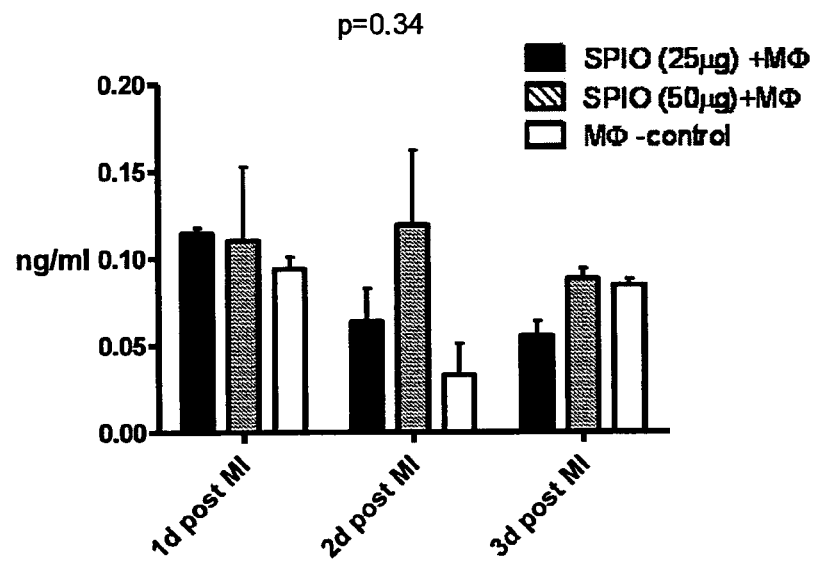
FIGS. 6A-6B are bar graphs showing IL-10 (FIG. 6A) and TGF-$\beta$ (FIG. 6B) secretion at different time points (1, 2, 3, 4 and 5 days) of incubation with peritoneal macrophages.
Figure 6B:
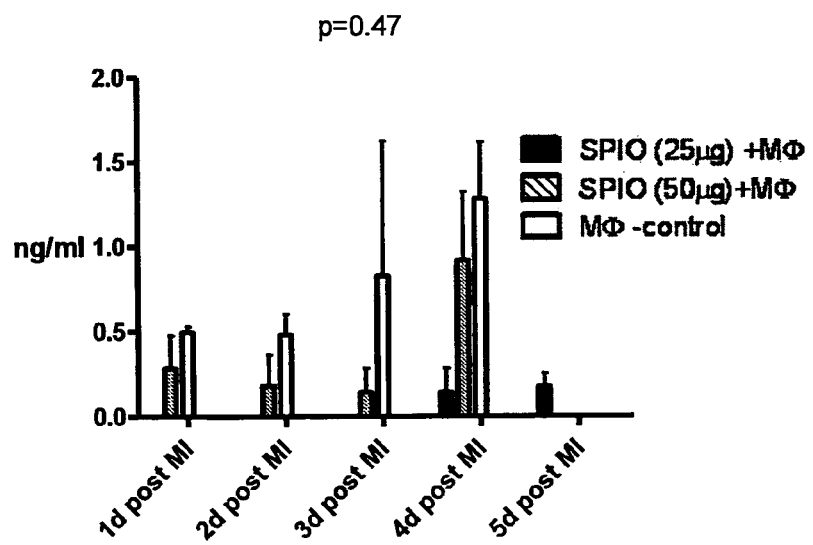

The addition of SPIO (25 and 50 μg) to peritoneal macrophage culture yielded near 100% phagocytosis. After one day, we found that both 25 and 50 μg of SPIO significantly reduced TNF-α secretion from the cultured macrophages, compared with controls (FIG. 5). While the effect of SPIO on IL-10 secretion from peritoneal macrophages was not remarkable (except on day 2 after treatment), SPIO attenuated the secretion of TGF-β, a pro-fibrotic factor, from cultured macrophages (FIG. 6).

SPIO Improves Heart Function after MI in Mouse

Figure 7A:
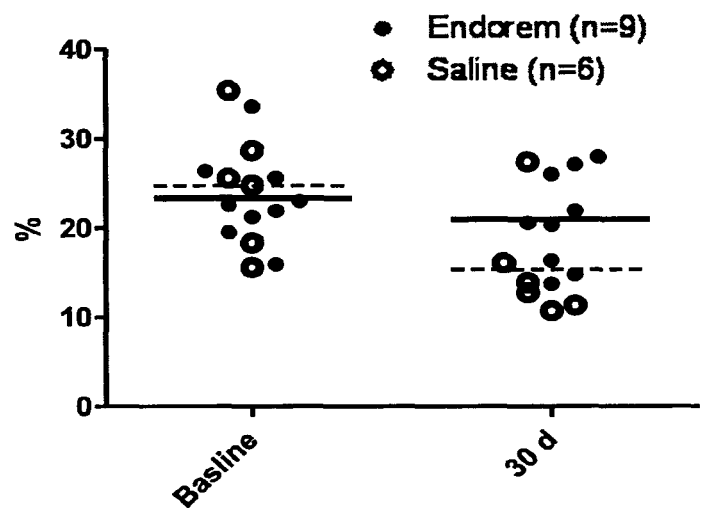
FIGS. 7A-7B are analysis of echocardiographs of mice treated with SPIO or saline after induction of MI in Balb C female mice.
Figure 7B:
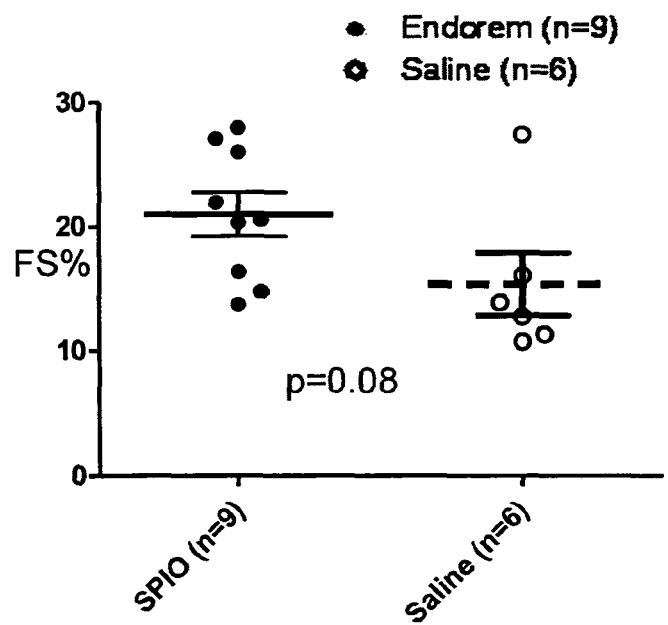

On echocardiography, animals treated by SPIO experienced greater LV fractional shortening (an index of contractility) compared with control animals one month after MI (FIGS. 7A-7B).

Specifically, FIGS. 7A-7B show that SPIO improved heart function after MI. Balb C female Mice (12 weeks, 20-25 g) were anesthetized with 2% isoflurane. The chest was opened by left thoracotomy through the fourth intercostal space to expose the beating heart. The left main coronary artery will be permanently occluded with an intramural suture. Ferumoxide (Endorem; Guerbet, Villepinte, France, provided with a total iron content of 11.2 mg/mL, 20 μl) or saline were injected into the infarcted mouse heart soon after coronary artery occlusion. Echocardiography studies were performed with the commercially available mouse echocardiography system (Vevo 770, VisualSonics) equipped with 35 MHz phased array at 1 and 30 days after MI. FIG. 7A shows the fractional shortening [FS=(left ventricle (LV) diastolic diameter−LV systolic diameter)/LV diastolic diameter] at baseline (1 day after MI) and 30 d after MI. There was an deterioration in fractional shortening in the control group and attenuation of the deterioration in the SPIO-treated animals. After 30 d, FS was greater in animals treated with SPIO compared with control (FIG. 7B; p=0.08). These results are indicative of tissue healing.

Results of Experiments in Rats

SPIO Delivered Intravenously into the Infarcted Myocardium

Thirteen rats underwent surgery to induce MI, and 9 underwent sham surgery. All rats were injected with either SPIO (18 mg/Kg of Endorem®; Guerbet, Villepinte, France) or the same volume of saline 0.9% 48 hours after the procedure. On days 6 and 10 they underwent MR imaging (0.5T GE iMRI). Imaging sequences included T1 spin echo and T2* gradient echo. The rats were then euthanized and the hearts processed for histology. Sections were stained with hematoxylin and eosin (H&E), iron staining for iron particle detection and immuno-labeled with antibodies against ED1 (Serotec), a marker for tissue-resident macrophages. Double staining for ED1 and iron was performed in order to establish that the iron was contained by macrophages. Hypo-intense signals were depicted on the MRI of the SPIO-injected rats with MI, and a correlation between the MRI and histology was found in some of the rats.

Of the 32 rats included in the study, 21 had an induced MI and the remainder underwent sham surgery. Six of the MI-induced rats died within 24 hours of the procedure. Two rats died within 24 hours of SPIO injection and 2 rats with MI had an unsuccessful injection due to technical difficulties. The final MRI and histological analysis included 13 rats with MI (7 injected with SPIO, 6 injected with saline) and 9 with sham surgery (5 injected with SPIO, 4 injected with saline).

Hypo-Intense Areas were Detected by MRI in Most Rats Treated by IV SPIO

Figures 8A, 8B, 8C, 8D:
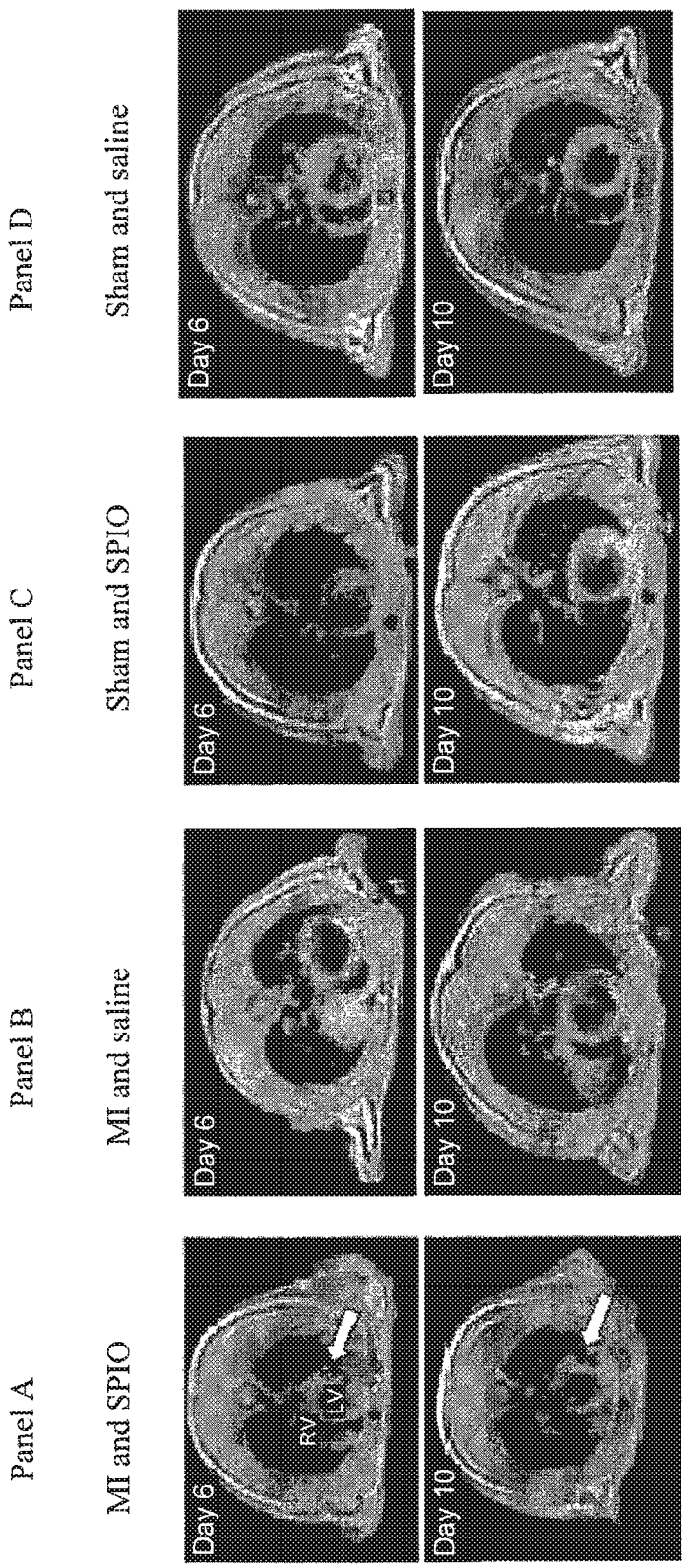
FIGS. 8A-8D are serial MRI scanning images at day 6 and 10 after MI identified SPIO uptake in an infarcted heart of rat, where
Figure 9A:
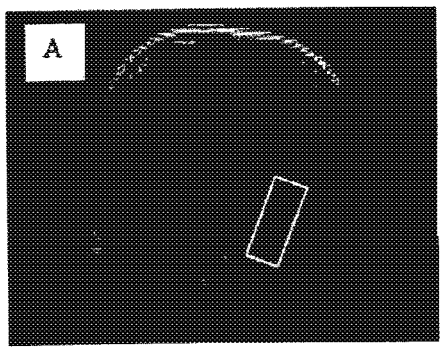
FIGS. 9A-9F are images showing that there is a good correlation between MRI iron signals and histology. Histologic correlation between the MI location on MRI (FIG. 9A) and low and medium power microscopy (ED1+iron staining—FIG. 9B & FIG. 9C) in specimens from a rat with MI and SPIO injection. When the suspected area is stained separately to iron (FIG. 9D) or ED1 (FIG. 9E)—the same areas are positively stained. Double staining (iron and ED1 staining) in high power shows that the iron is contained by macrophages
Figure 9B:
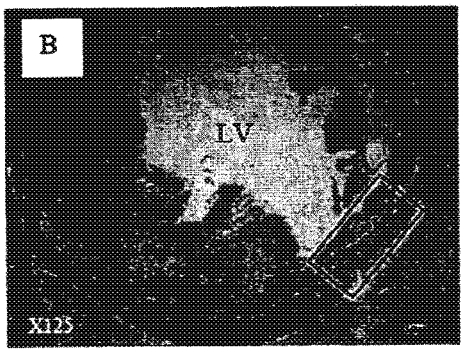
Figure 9C:
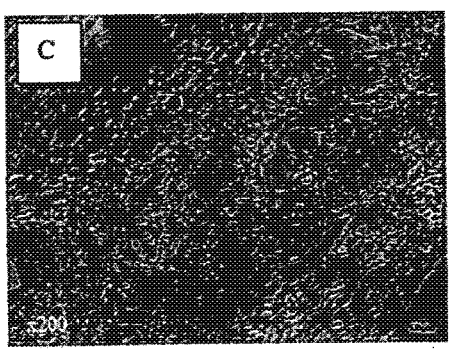
Figure 9D:
Figure 9E:
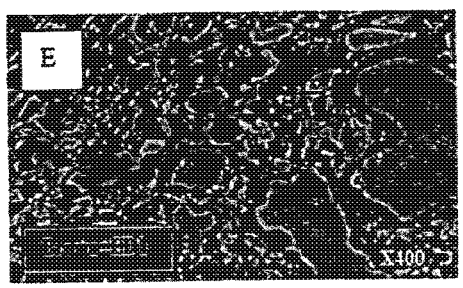
Figure 9F:

All MR images were analyzed by a senior experienced MR imaging researcher in an unbiased manner in order to point out the suspicious areas containing SPIO. Hypointense areas were detected in most of the SPIO-injected rats with MI (FIG. 8, panel A). The signal was persistent in position on the two scans performed at days 6 and 10. Conversely, on the MR images of rats with MI injected with saline (FIG. 8, panel B), we found evidence of MI demonstrated by decreased wall thickness of the LV, with no persistent signal indicating SPIO presence. Rats that had undergone sham surgery and were injected with SPIO (FIG. 8, panel C) also demonstrated different inconsistent artifacts and demonstrated normal LV wall thickness. As expected, sham-operated rats without SPIO injection (FIG. 8 panel D) had normal LV wall thickness and no signals suspicious of SPIO presence.

Good Correlation Between MRI Signal for Iron and Histological Findings

H&E staining confirmed the existence of MI in the relevant rats. Positive staining for both iron and ED1 was evident in all the MI-induced rats in the same area seen on the MRI. Analysis of the double staining (ED1 and iron) indicated a stronger double staining pattern in some of the rats who had an MI and were injected with SPIO (FIG. 8). In MI-induced rats without injected SPIO, there was also positive staining for ED1 but significantly less positive staining for iron. All the sham-operated animals were negatively stained for iron with a few ED1 signals (without double staining) (FIG. 8). There was a good correlation between the MRI signal for iron and histological findings of iron-loaded macrophages (FIG. 9).

Results of Experiments in Human Macrophages

The Effect of IONPs on Macrophage Polarization

Figure 10A:
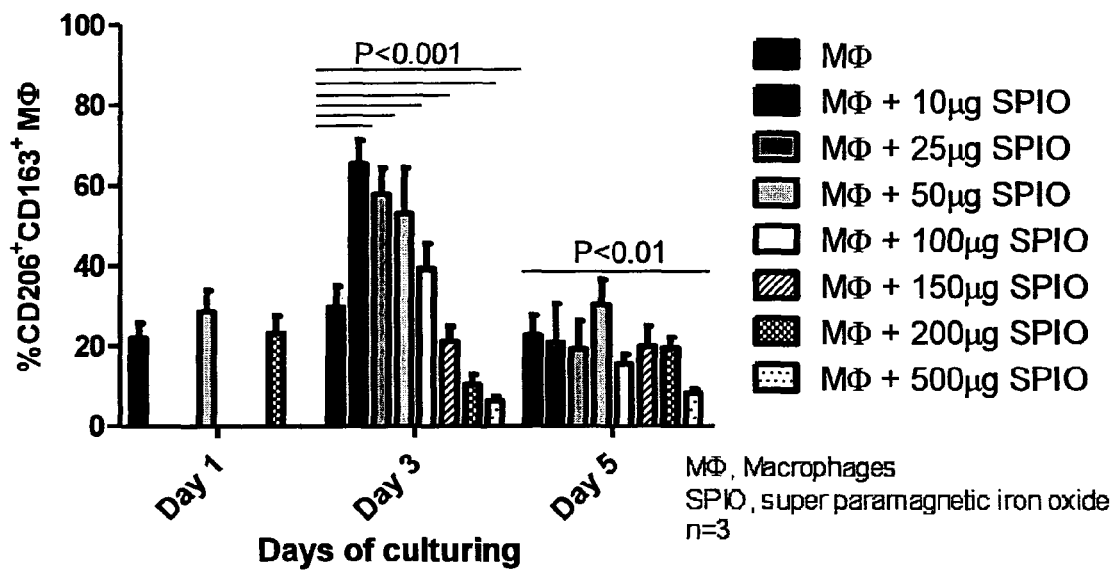
FIGS. 10A-10B are graphs showing that the percentage of macrophages expressing M2 markers (CD206 and CD163) increases after incubation with low doses of SPIO (10-100 µg) and decreases after incubation with high doses of SPIO (FIG. 10A), especially after incubation of SPIO for three days (FIG. 10B).

Incubation with SPIO doses lower than 100 µg increased the percentage of macrophages expressing M2 markers, CD206 and CD163 (up to 2.5-fold, p<0.001, FIG. 10A), especially after three days of incubation. Higher doses of SPIO decreased the percentage of macrophages expressing M2 markers CD206 and CD163 (up to 3-fold, p<0.01). CD206 and CD163 are markers of anti-inflammatory M2-type human macrophages.

Figure 10B:
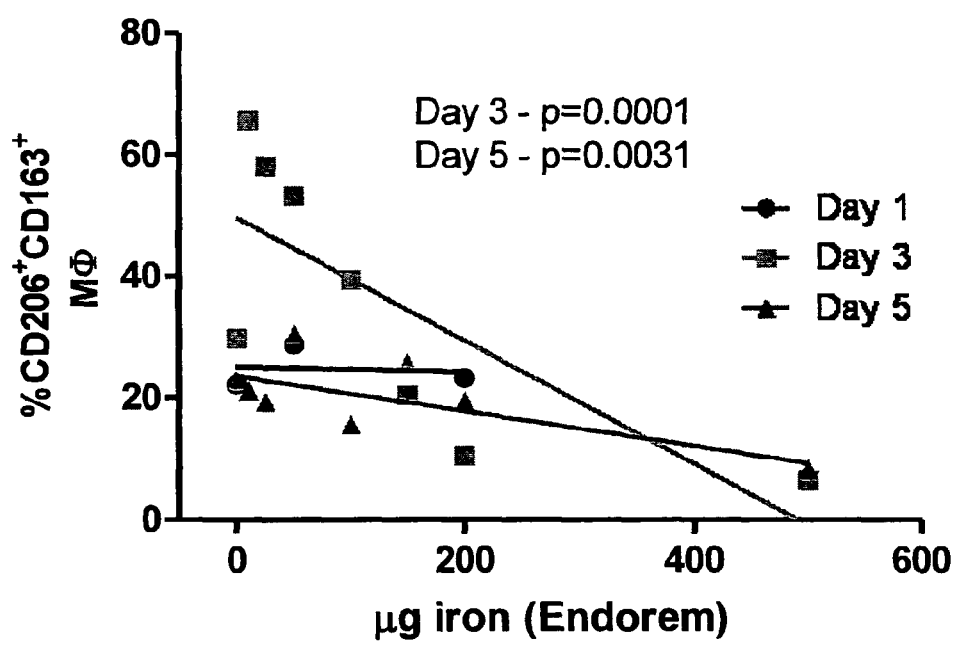

These results show that IONP have a dose-dependent bipolar effect on macrophages polarization mostly after 3 days of incubation (FIG. 10B).

The effect of IONPs on cytokine secretion of macrophages

Figure 11A:
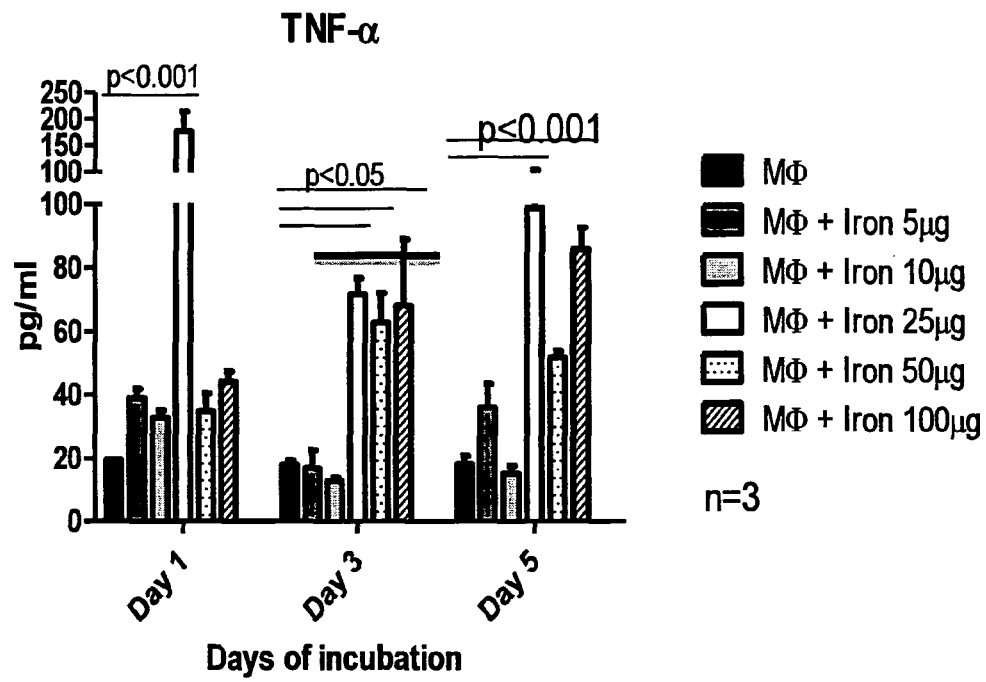
FIGS. 11A-11N are bar graphs showing the profile of cytokine secretion by macrophages after incubation with different concentrations of IONs (5 µg, 10 µg, 25 µg, 50 µg, 100 µg) for 1 day, 3 days and 5 days.
Figure 11B:
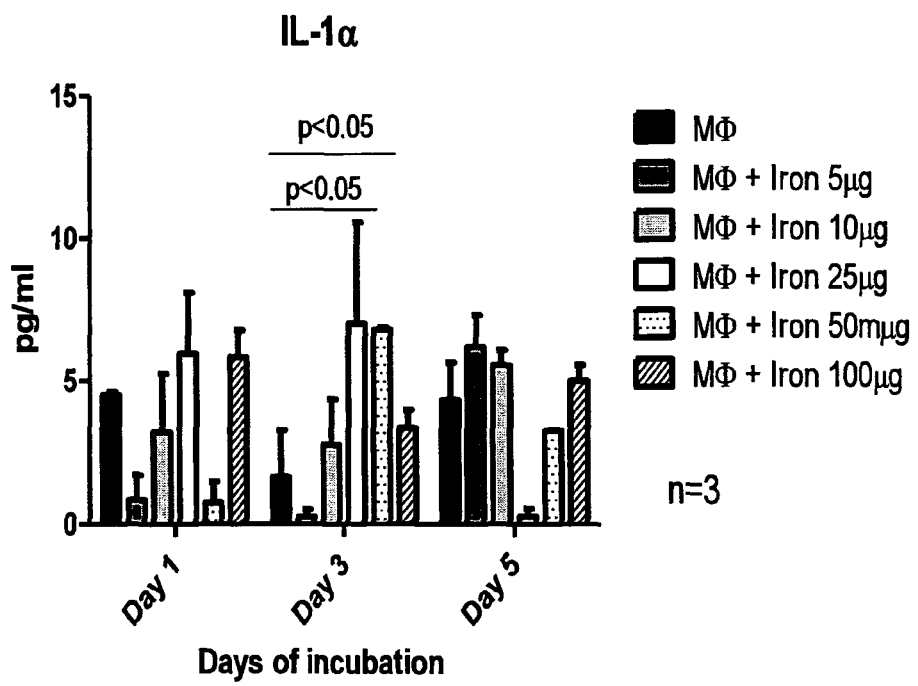
Figure 11C:
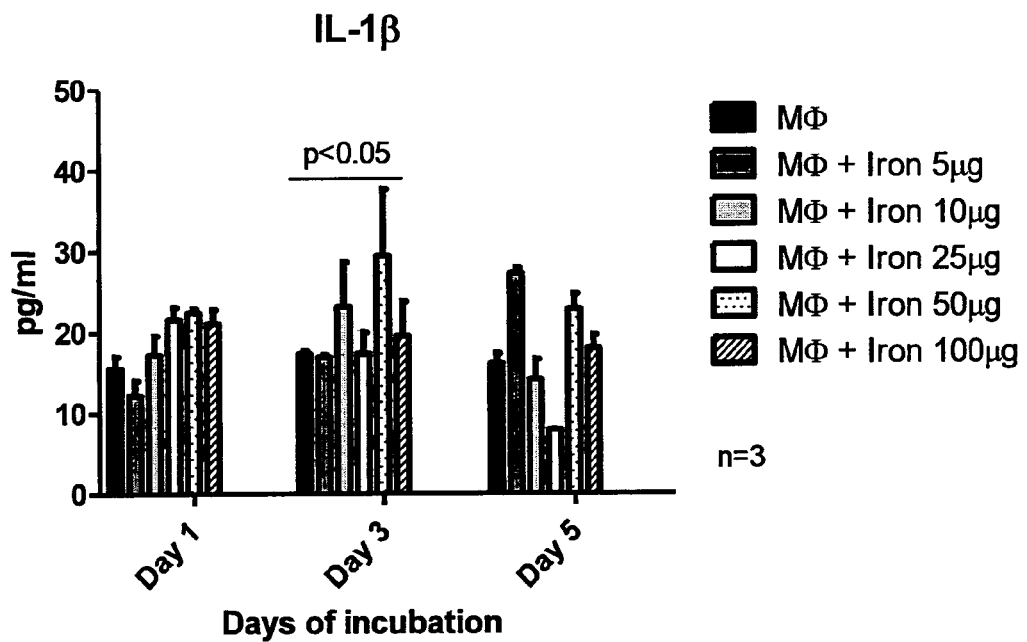
Figure 11D:
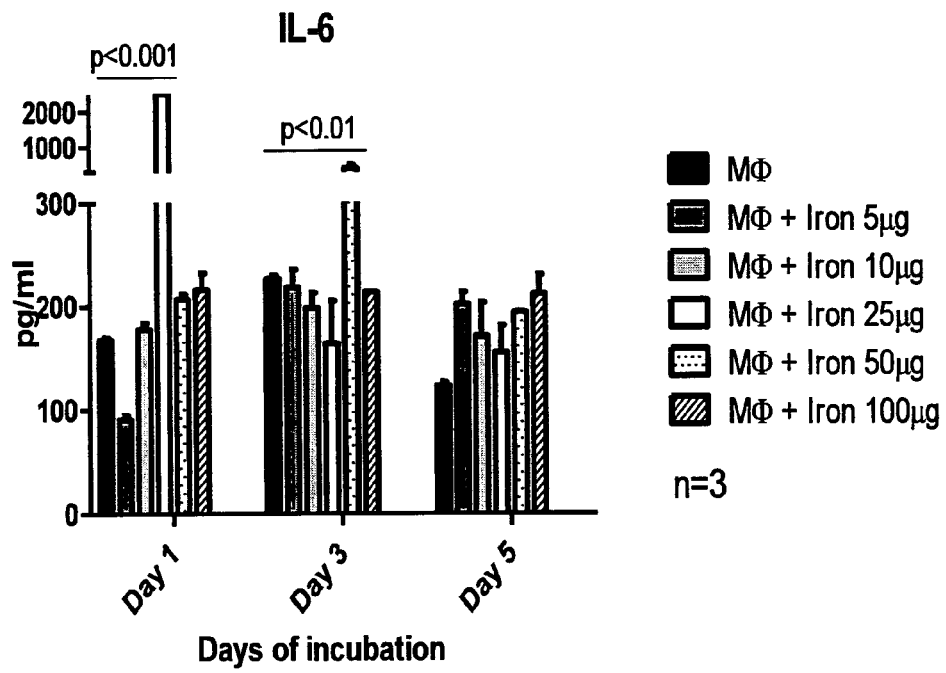
Figure 11E:
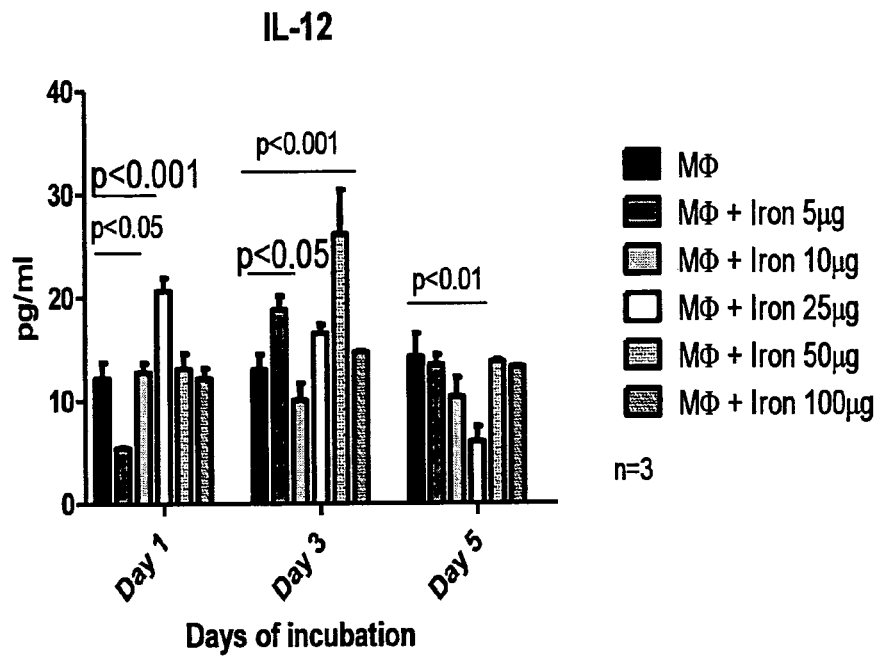
Figure 11F:
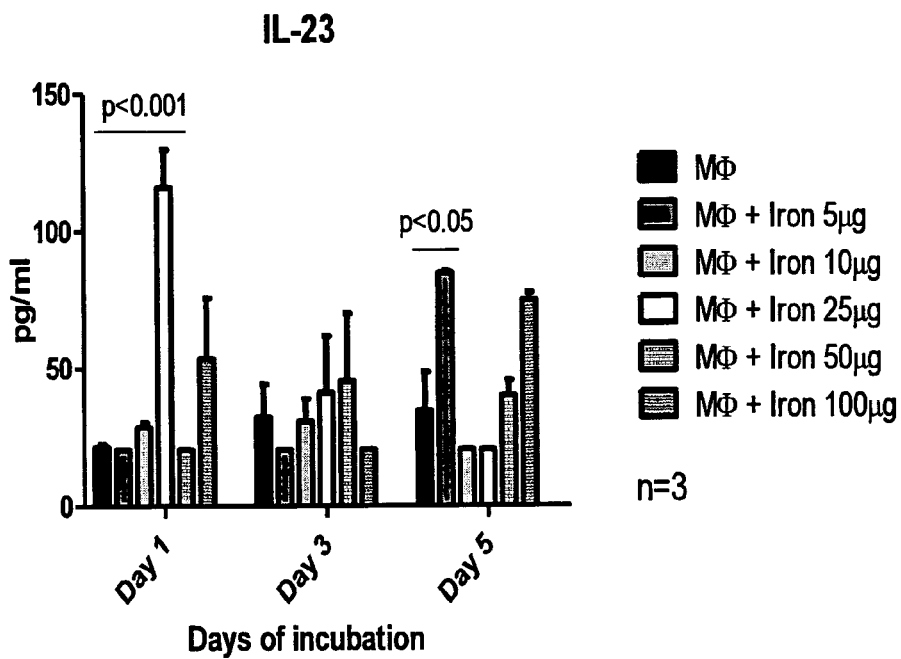
Figure 11G:
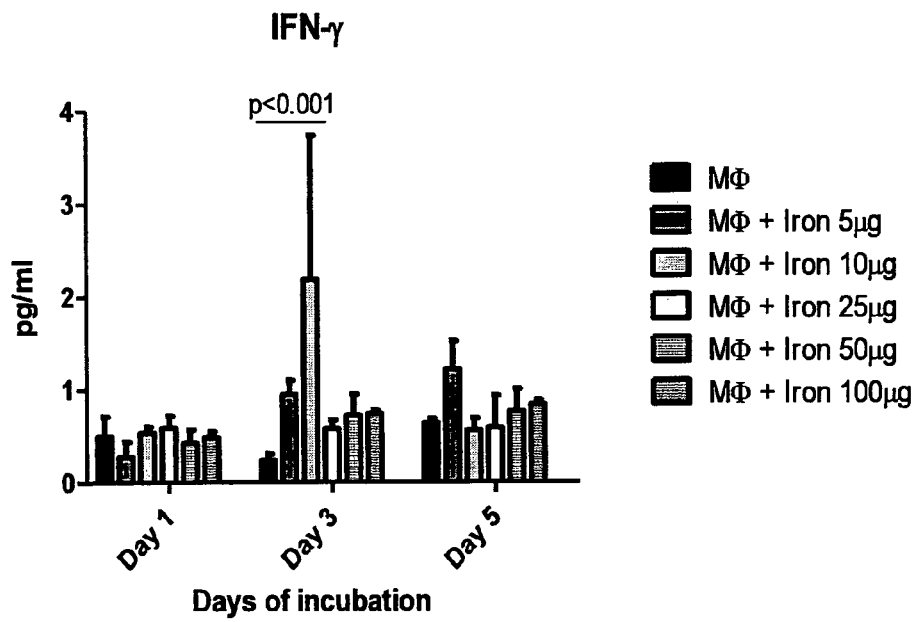
Figure 11H:
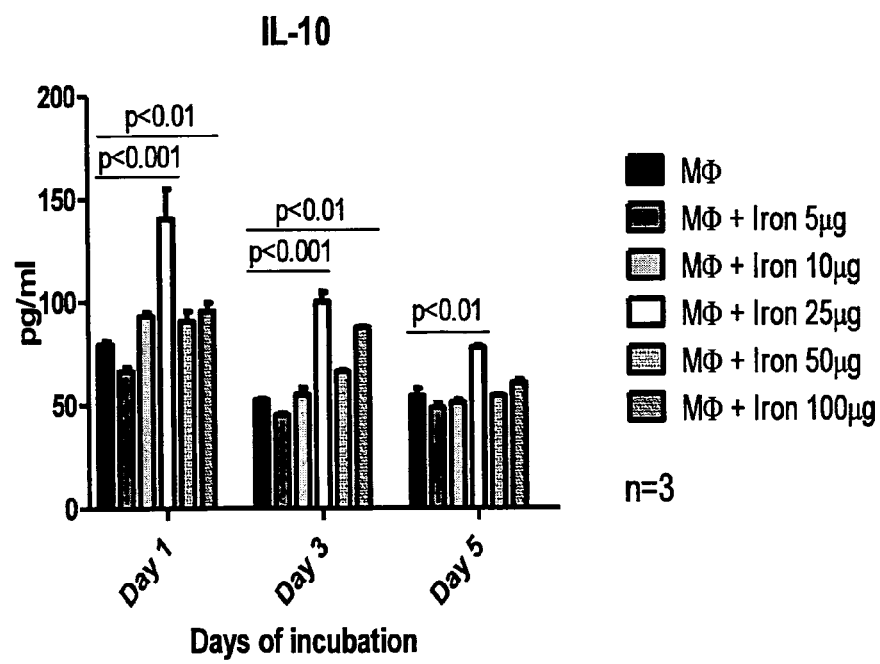
Figure 11I:
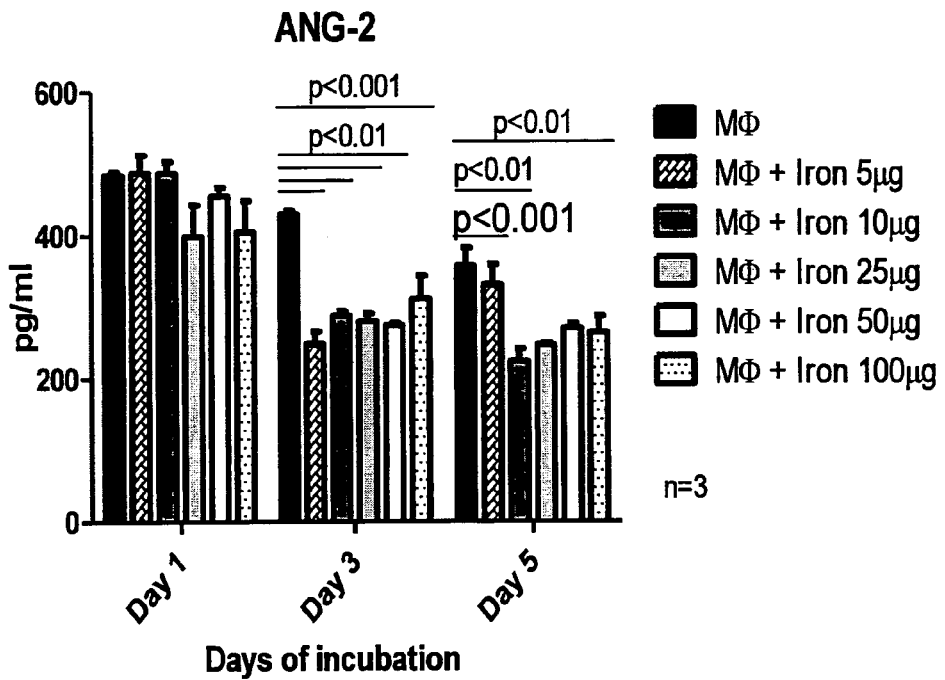
Figure 11J:
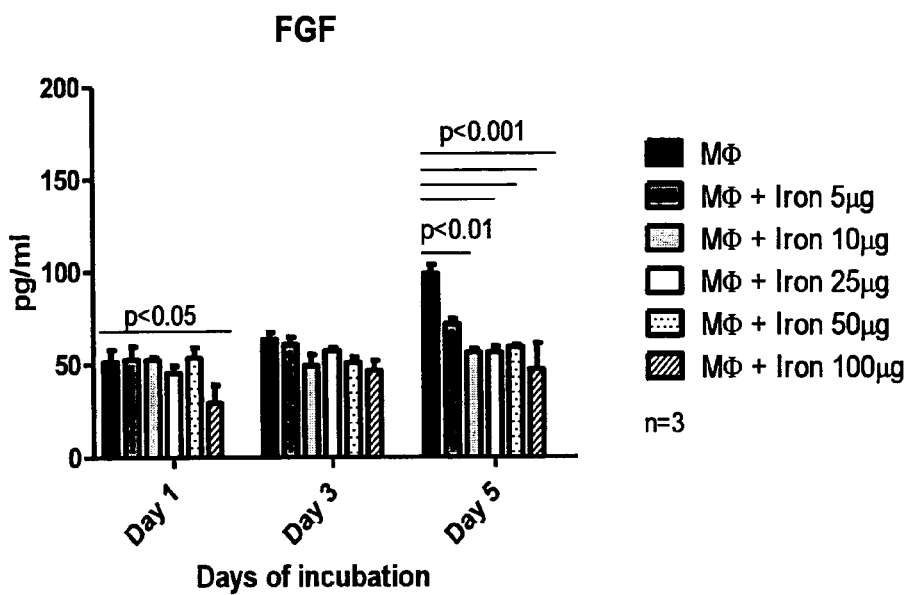
Figure 11K:
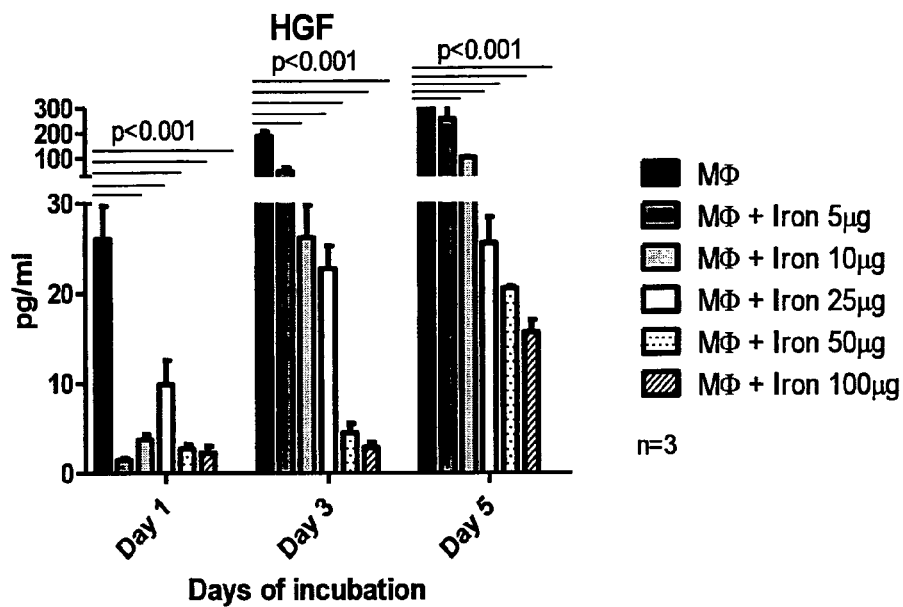
Figure 11L:
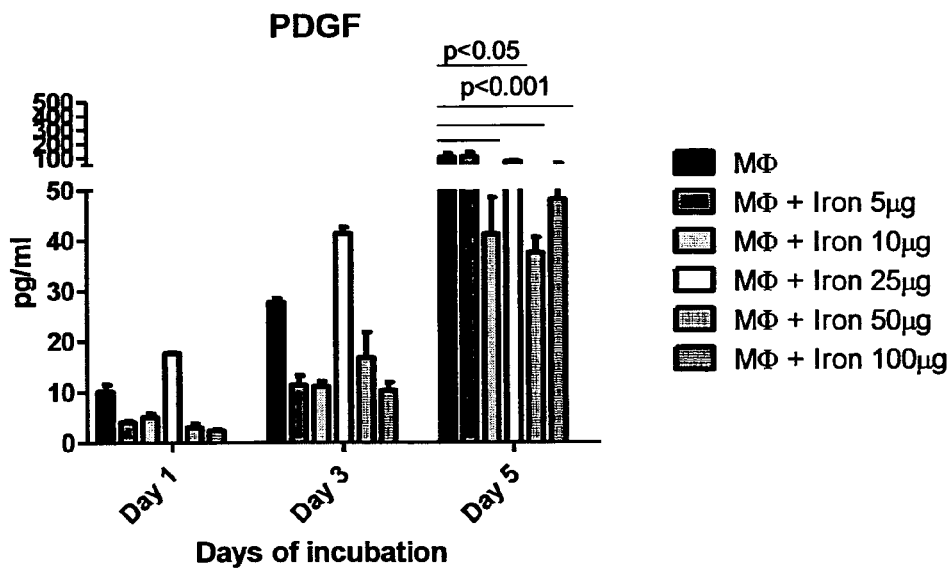
Figure 11M:
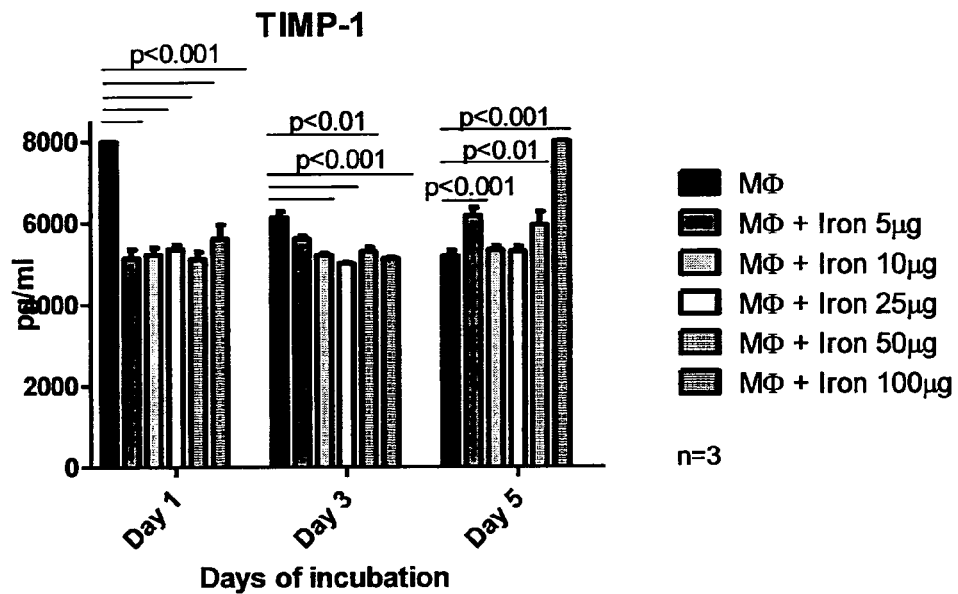
Figure 11N:
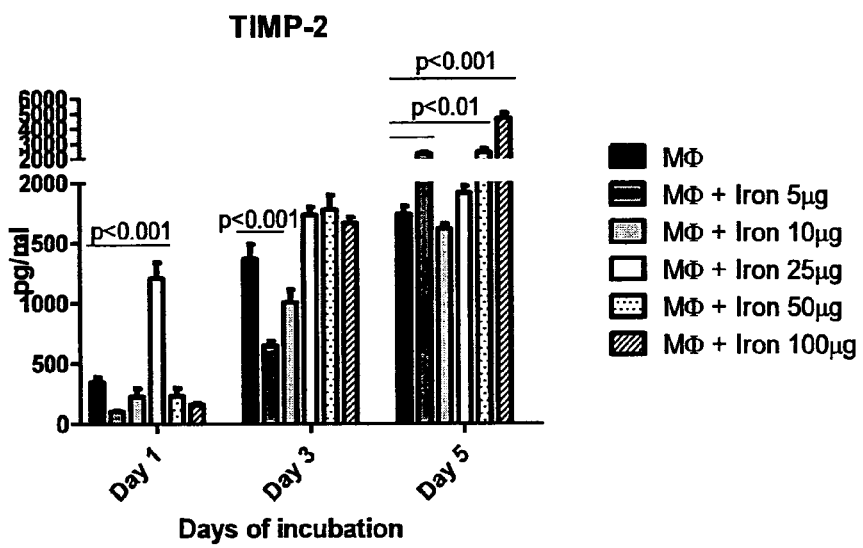

The profile of cytokines secretion of macrophages following incubation with IONPs is shown in FIGS. 11A-11N.

Specifically, incubation of macrophages with low doses of IONPs (25-50 µg) increased macrophage secretion of M1-associated inflammatory cytokines TNF-α (TNFα being typical for both M1 and M2b, up to 9-fold) (FIG. 11A), IL-1α and IL-1β (up to 4-fold) (FIGS. 11B-11C, respectively), IL-6 (IL-6 being considered typical for both IL-6 M1 and M2b and induce M2) (up to 1.5-fold) (FIG. 11D), IL-12 (up to 2-fold) (FIG. 11E), IL-23 (up to 5-fold) (FIG. 11F), and INF-γ (up to 9 fold) (FIG. 11G).

In addition, incubation of macrophages with low doses of IONPs (25-50 µg) increased M2-associated anti-inflammatory IL-10 (up to 2-fold) (FIG. 11H).

On the other hand, IONPs decreased macrophage secretion of angiogenic cytokines typical to M2 such as: ANG-2 (up to half (1.5 fold)—(FIG. 11I)), FGF ((up to half (1.5 fold) (FIG. 11J)), HGF (up to 20 times) (FIG. 11K), platelet-derived growth factor (PDGF) (up to 2.5 times) (FIG. 11L) and TIMP-1 (up to by 36%) (FIG. 11M), TIMP-2 (up to third) (FIG. 11N). The largest effect occurred on day 3 of incubation, mostly in the 25/50 µg IONP groups.

After, incubation of macrophages with high doses of IONPs (75-100 µg), the augmentation effects, on M1 and M2 associated cytokines, significantly decreased (FIG. 11).

The Profile of cytokine secretion by macrophages is provided in FIGS. 11A-11N and are obtained from Multiplex ELISA, the cytokines amounts are provided in pg/ml. Mφ—human macrophages. The secretion of IL2, IL4, IL-5, IL-8, IL-13, IL-15, IL-17, VEGF was not affected by treatment of IONP.

IONPs induce morphological changes in macrophages

Figure 12A:
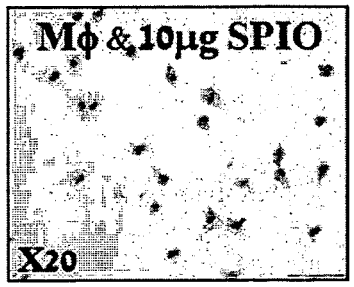
FIGS. 12A-12E are images showing that SPIO induced morphological changes in macrophage's shape in a dose and a time dependent manner.
Figure 12B:
Figure 12C:

Incubation of macrophages with 10 µg, 50 µg and 100 µg IONP for one, three and five days showed that IONP induces morphological changes in macrophages in a dose and time dependent manner. Specifically, as shown in FIGS. 12A-12C, on day 1, incubation with 100 µg IONP changed macrophage morphology to a bigger and rounder shape, with darker cytoplasm (filled with IONPs).

Figure 12D:
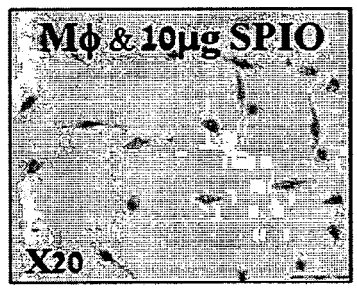
Figure 12E:
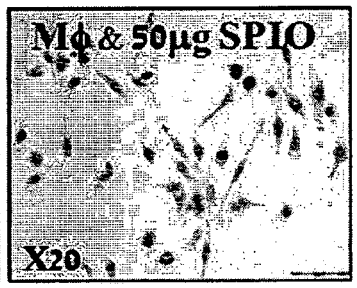
Figure 12F:
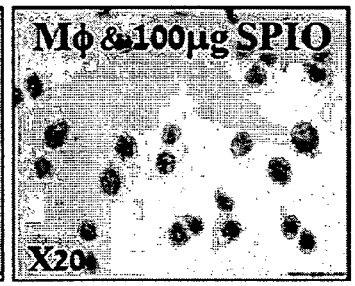
Figure 12G:
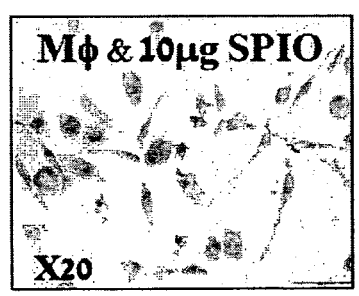
FIGS. 12G-12I macrophages incubated for five days with 10 μg, 50 μg, 100 μg, respectively; the change in the morphology of the macrophage comprise a more round cell shape comprising darker gold-brown cytoplasm filled with iron particles and less cytoplasmic extensions. This morphology was observed in M2-polarized-macrophages.
Figure 12H:
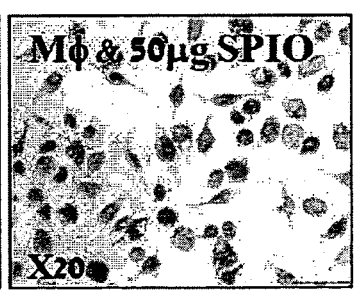
Figure 12I:
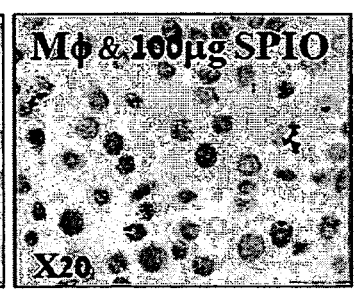

This change in morphology is more substantial when macrophages are incubated with 50 µg and 100 µg IONP for 3 days (FIGS. 12D-12F) and for 5 days (FIGS. 12G-12I)

These results suggest that macrophages have a large capacity for engulfing high doses of IONPs, up to a point when the cytoplasm is filled to its maximum and the nucleus is forced up against the cell membrane (FIG. 12I).

IONPs effect on the phagocytic capacity of macrophages

Figure 13:
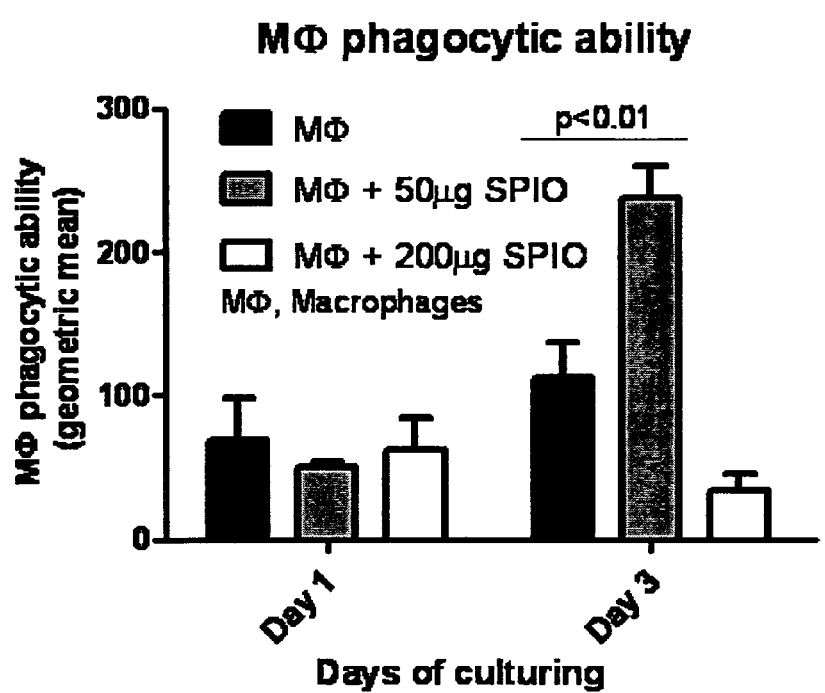
FIG. 13 is a bar graph showing that SPIO's induces a bi-polar effect on the phagocytic ability of macrophages; incubation for three days of macrophages with 50 μg SPIO's increased the ability of macrophage phagocytic, whereas incubation with 200 μg SPIO's decreased this ability.

Incubation of macrophages with 50 µg IONPs for 3 days increased the phagocytic ability of macrophages (2-fold, p<0.01, FIG. 13), whereas incubation with 200 µg IONPs decreased this phagocytic ability (3-fold, FIG. 13).

No changes were observed in the phagocytic ability of the macrophages after one day of incubation with both doses of 50 µg and 200 µg.

The changes in phagocytic ability was determined from the change in the number of red fluorescent latex beads which were phagocytised per cell, measured by the fluorescent intensity mean of the macrophages which phagocytised beads.

Wound Healing in Mice

Wound healing in mouse treated with topical IONP (20 µl of 0.224 mg IONP, 0.2 M) (n=4) was significantly faster and more complete, compared with mouse treated with topical saline (n=2), as measured after 12 days. These results indicated that administration of IONP improve wound healing.

Figure 14A:
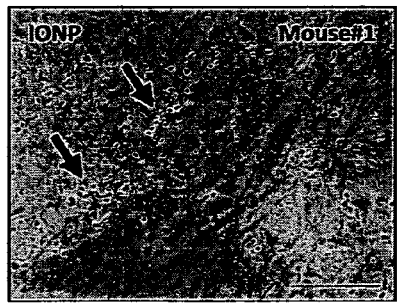
FIGS. 14A-14E are images showing histological staining of Prussian blue for iron particles (indicated by arrows) of back biopsy sections.
Figure 14B:
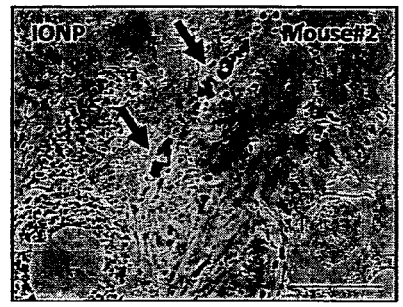
Figure 14C:
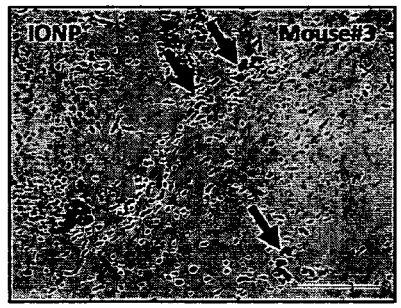
Figure 14D:
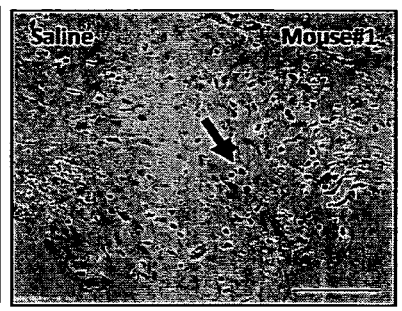
Figure 14E:
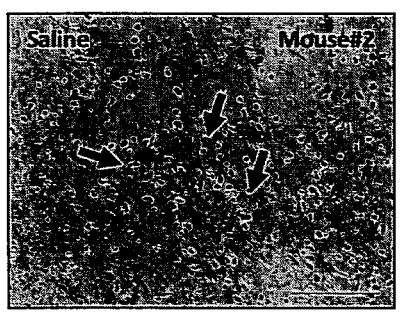

Histological analysis of the wound biopsies using Prussian blue staining for iron particles detection (Sigma Aldrich, Rehovot, Israel) indicated no differences between IONP-treated mice (FIG. 14A-14C, the arrows indicating the Prussian blue staining for iron particles detection) and saline-treated mice (FIGS. 14D and 14E).

Liposome targeting

The targeting ability of different liposomal systems was evaluated (Table 1). Macrophages, as part of their natural functions, phogocytose/internalize particles, showing preferences to the micro-sized over the nano-sized systems. This can be utilized for targeting drugs to macrophages, as demonstrated and supported by the data shown here. Regular ULV (RL-ULV) and Hyaluronic acid coated ULV (HA-ULV), being two nano-sized liposomes (see diameters in Table 1) show poor to medium affinity to the macrophages. Confocal microscopy studies showed hardly any RL-ULV at the macrophage surface and few HA-ULV at the macrophage surface (by imaging). RL-MLV and HA-MLV, the two micro-sized liposomes (see diameters in Table 1) were distinctly different from the nano-sized liposomes, as well as from each other. Both bind to the macrophages with high affinity, the RL-MLV to scavenger receptors at the macrophages surface, and the HA-MLV to the hyaluronan receptors (particularly the CD44 family) at the macrophage surface. By confocal microscopy studies it was further found that the RL-MLV bound to the macrophage surface and were also internalized, the macrophage interior filled with the liposomes. The HA-MLV, on the other hand were well-bound to the macrophage membrane; but were not internalized.

TABLE 1

Targeting liposomes to macrophages

| Liposomal system | Hydrodynamic diameter (nm) | Macrophage Binding affinity | Internalization |
|---|---|---|---|
| RL-ULV | 124(±6) | Poor | No |
| HA-ULV | 192(±8) | Medium | No |
| RL-MLV | 2340(±10) | High | Yes |
| HA-MLV | 2340(±10) | High | No |

It is noted that "RL" indicates regular liposomes, accordingly RL-ULV and RL-MLV are regular uni and multilamellar liposomes, respectively. HA indicated hyaluronan coating the liposomal surface (by covalent attachment), accordingly HA-ULV and HA-MLV are hyaluronan-coated uni and multilamellar liposomes, respectively. The internalization is of the liposomes—intact liposomes, hence anything inside the liposomes will also be internalized.

The invention claimed is:

1. A method for treating myocardial infarction in a human subject suffering from myocardial infarction, the method comprising:
administering to the subject in need an amount of an active agent effective to treat myocardial infarction, said active agent being iron oxide nanoparticles,
wherein said method does not include a step of magnetic resonance imaging of myocardial infarction using iron oxide particles.

2. The method of claim 1, wherein the iron oxide nanoparticles are in naked form, surface modified, or formulated within a carrier.

3. The method of claim 1, wherein the iron comprises one or both of ferric iron ($Fe^{3+}$) and ferrous iron ($Fe^{2+}$).

4. The method of claim 1, wherein the iron oxide is selected from the group consisting of magnetic iron oxide, ferromagnetic iron oxide, ferrimagnetic iron oxide and antiferromagnetic iron oxide.

5. The method of claim 1, wherein the iron oxide is superparamagnetic iron oxide.

6. The method of claim 1, wherein the iron oxide nanoparticles are modified with an organic material selected from the group consisting of small molecules, surfactants, polymers and biomolecules.

7. The method of claim 1, wherein the iron oxide nanoparticles are modified with an inorganic material selected from the group consisting of silica, metal substance, non-metal elementary substance, metal oxides and metal sulfides.

8. The method of claim 1, wherein the iron oxide nanoparticles are in the form selected from the group consisting of an iron oxide core within a shell of organic or inorganic material; a mosaic form; a core of organic or inorganic material within a shell of iron oxide; a shell-core-shell form; and a bi-functional dumbbell form.

9. The method of claim 1, wherein the iron oxide nanoparticles are embedded within a polymeric shell coating or encapsulated within a core or a lipid-based vesicle.

10. The method of claim 9, wherein the iron oxide nanoparticles are encapsulated within liposomes.

11. The method of claim 10, wherein the liposomes are multilamellar vesicles (MLV).

12. The method of claim 10, comprising a targeting moiety for targeting the liposome to a target site.

13. The method of claim 12, wherein the targeting moiety is hyaluronic acid.

14. The method of claim 9, wherein the polymeric shell coating comprises polymers selected from the group consisting of polysaccharide, polyethyleneglycol, dextran, siloxanes, and carboxydextran.

15. The method of claim 1, wherein the iron oxide nanoparticles have a diameter of between 1 nm to 200 nm.

16. The method of claim 1, wherein the iron oxide nanoparticles are administered by injection in combination with a pharmaceutical carrier.

* * * * *